United States Patent [19]
Bittner et al.

[11] Patent Number: 5,506,350
[45] Date of Patent: Apr. 9, 1996

[54] PRODUCTION OF CHROMOSOME REGION SPECIFIC DNA SEQUENCES AND TRANSAMINATION

[76] Inventors: Michael L. Bittner, 1768 Brookdale Rd., Naperville, Ill. 60563; Lucy M. Stols, 1518 Darien Lake Dr., Darien, Ill. 60559; Clarissa F. Prorok, 133 Sandalwood Dr.; Kenneth A. Cruickshank, 128 Robin Hill Dr., both of Naperville, Ill. 60540

[21] Appl. No.: 109,167

[22] Filed: Aug. 19, 1993

Related U.S. Application Data

[63] Continuation of Ser. No. 762,912, Sep. 19, 1991, abandoned, which is a continuation-in-part of Ser. No. 585,876, Sep. 20, 1990, abandoned.

[51] Int. Cl.$^6$ ............................... C07H 5/04; C07H 5/06
[52] U.S. Cl. .................... 536/55.3; 536/55.1; 536/25.32; 536/23.1
[58] Field of Search .................... 536/55.3, 55.1, 536/23.1, 25.32; 435/6

[56] References Cited

FOREIGN PATENT DOCUMENTS 8706621  11/1987  WIPO.

OTHER PUBLICATIONS

Draper, Nucleic Acid Res 12:989–1002 (1984) "Attachment of Reporter groups to specific . . . ".

*Primary Examiner*—W. Gary Jones
*Assistant Examiner*—Eggerton Campbell
*Attorney, Agent, or Firm*—William E. Murray

[57] ABSTRACT

Techniques for producing cloned DNA sequences are provided which sequences are complementary to DNA occurring in one selected region of one chromosome of a multi-chromosomal genome, such as the human genome. Such cloned DNA sequences can be labeled and formed into probes by conventional procedures, there are provided methods for making probe compositions which comprise mixed DNA segments derived from such a DNA sequence. An improved DNA sequence transamination procedure is provided utilizing trifluoroacetate chaotrope anions. With high concentrations of low complexity DNA, high levels of transamination are thereby achieved. These segments are covalently bound to fluorophore groups through linking groups that are transaminated preferably chaotropically into the segments.

12 Claims, No Drawings

5,506,350

PRODUCTION OF CHROMOSOME REGION SPECIFIC DNA SEQUENCES AND TRANSAMINATION

RELATED APPLICATION

This is a continuation of application Ser. No. 07/762,912, filed Sep. 19, 1991, abandoned, which is a continuation-in-part of earlier filed U.S. patent application Ser. No. 585,876 filed Sep. 20, 1990, abandoned, by M. L. Bittner, L. E. Morrison and M. S. Legator.

FIELD OF THE INVENTION

This invention relates to cloned DNA sequences that are specifically complementary to prechosen target regions within individual chromosomes of a genome which is typically multi-chromosomal, to processes for making the same, to processes for producing probes therefrom and to usage of such probes.

BACKGROUND OF THE INVENTION

Probes containing DNA sequences which are complementary to specific chromosomal alphoid DNA are known to be useful as enumerators in in situ hybridization assays. The best known members of the prior art alphoid DNA sequences preparation methods use a common approach for isolating the alphoid DNA sequences. An enrichment based on a physical characteristic of repeated DNA is applied, DNA from the enriched pool is cloned and individual clones from this enriched pool are individually analyzed for utility in in situ hybridization assays. Searching such a pool has proven to be an inefficient and unreliable method for obtaining a sequence with high chromosomal specificity for a predetermined chromosome. The first such scheme to obtain cloned alphoid DNA used the buoyant density characteristics of alphoid DNA to produce an enriched pool of DNA sequences. (See Manuelidis, L., et al. in *Chromosoma* 66:23–32 (1978)). Other schemes for obtaining alphoid DNA clones have used the distribution of DNA restriction sites or the rapid renaturation of alphoid DNA relative to non-repeated species in the genome as the basis for producing enriched pools of alphoid DNA. (See Yang, T. P., et al., *Proc. Natl. Acad. Sci. USA.* 79:6593–6597 (1982), and Moyzis, R. K., et al., *Chromosoma* 95:375–386 (1987)). However, these methods are inherently relative inefficient and are not well suited for rapid commercial development of enumerator probes.

Also, prior art probes prepared from such sequences were indirect label probes and so required post-hybridization processing in order to achieve hybrid detection in contrast to direct label probes which require, for example, only one probe penetration step of a slide mounted specimen during in situ hybridization. Indirect label probes require the successful diffusion into the slide mounted specimen of the various protein reagents (antibodies, avidins, enzymes and the like) during an in situ hybridization multi-step procedure.

Prior art methods for labeling such prior art chromosome regionally specific complementary DNA sequences present difficulties in controlling the number of label moieties attached to individual sequences.

Improved DNA segments which are complementary to specific chromosomal DNA repeated segments existing in a particular chromosomal region, such as, for example, alphoid DNA in a specific chromosome, and improved methodology for making direct labeled probes therefrom, would be very useful. The present invention provides both such segments and such methodology.

SUMMARY OF THE INVENTION

This invention provides (a) a new and very useful class of cloned DNA sequences which incorporate DNA repeated segments and which are specifically complementary to prechosen regions of individual chromosomes of a genome which is typically multi-chromosomal, and (b) processes for making and for converting same to probe compositions, especially chaotropic transamination.

The invention avoids the problem of individually testing large numbers of clones derived from a large pool and enhances the capacity to produce specific sequences which are complementary to a desired prechosen chromosome.

More particularly, in one aspect, the present invention provides (a) methodology for making individual cloned DNA sequences which incorporate DNA repeated segments and which are complementary to sequential DNA sequences that occurs uniquely in only one selected region of one selected chromosome of a multi-chromosomal genome, and (b) the cloned DNA sequences so made. This methodology utilizes specific combinations of:

(a) enzymatic amplification of template DNA that is comprised of DNA sequences which together comprise a selected starting single whole chromosome of a multi-chromosomal genome using as primers synthesized oligonucleotides that are known to exist commonly and repetitively within or between adjacent DNA repeated segments which are present in one selected region in such template chromosome;

(b) clone colony production and sampling using either the so enzymatically amplified DNA repeated segments or DNA repeated segments separated from genomic DNA after identification thereof by hybridization using probes formed with the so enzymatically amplified DNA repeated segments; and (c) hybridization of probes formed by labeling sampled, cultured and extracted colony-derived vector DNA sequences with selected samples of genomic DNA target sequences.

From the resulting hybrids, at least one individual cloned DNA sequence is selected that contains a plurality of copies of at least one DNA repeated segment that occurs in, and that is complementary to, a DNA sequence or sequences which occur(s) in the one selected region of the selected starting single chromosome. Each selected cloned DNA sequence is then cultured to produce a plurality of replicates thereof.

Thus, the present invention provides a new class of cloned DNA sequences wherein each sequence produced as indicated above is complementary to a preselected one region of a preselected chromosome. Also, each such sequence contains at least one DNA repeated segment which occurs in such one region.

These novel cloned and replicated DNA complementary sequences can be labeled to produce new and useful probes for hybridization assays of specimens for which karyotypic information is desired. In general, probes produced from these cloned DNA sequences can be classified as repeat sequence based probes.

In another aspect, the present invention provides methodology for making intermediates useful in the production of direct label probe compositions. The methodology uses as starting materials (1) at least one starting DNA sequence such as taught herein, (2) linking group compounds and (3) fluorophore group containing compounds. This probe composition-making methodology preferably utilizes a combination of:

(a) fragmenting of the starting DNA sequence(s) into DNA segments;

(b) transaminating the DNA segments to introduce linking groups thereinto; and (c) covalently bonding fluorophore groups to the so introduced linking groups.

In a present transamination procedure, the linking compound is difunctional. One functional moiety thereof is an amino group, the other a group that is reactive with another reactive group that is present in the starting fluorescent compound. This transamination procedure is conducted under aqueous liquid phase, ambient temperature conditions in the presence of a bisulfite catalyst. Controlled transamination of the deoxycytidine nucleotides present in the selected regional DNA sequences and/or fragments thereof is accomplished without otherwise substantially altering sequence structure or complementary character so that the resulting transaminated polynucleotides retain their capacity to hybridize to complementary target DNA sequences that incorporate the segments in the selected chromosomal region.

In another aspect of the present invention, a novel transamination technique is provided by which polynucleotides are maintained in a single stranded condition during such a transamination procedure. This technique utilizes the presence of trihaloacetate chaotrope anions in the bisulfite catalyzed aqueous reaction medium together with the reactants. Such chaotrope anions induce and, particularly, maintain, nucleotide sequence denaturation as desired during the transamination without inducing crystallization of reactants and without reacting with reactants. This technique is also advantageous because it permits synthesis of relatively large batches of transaminated DNA sequences and/or segments, if such are desired, without the high cost and low reliability of prior art enzymatic labeling methods.

A class of new and very useful transaminated DNA segments is produced by the indicated chaotropic bisulfite catalyzed transamination procedure.

Direct label probe compositions particularly those prepared from such new class of chaotropically transaminated segments display excellent hybridization capacity and the hybrids produced thereby have excellent signal strength production capability.

Other and further features, objects, aims, purposes, advantages, applications, embodiments and the like will be apparent to those skilled in the art from the teachings of the present specification taken with the accompanying drawings.

DETAILED DESCRIPTION (A) Definitions

The term "sequence" refers to a chain or interconnected series of DNA nucleotides.

The term "fragment," "segment" or "DNA segment" indicates generally only a portion of a larger DNA polynucleotide or DNA sequence such as occurs in one chromosome or one region thereof. A polynucleotide, for example, can be broken up, or fragmented into, a plurality of segments.

The term "DNA repeated segment" refers to the fact that a particular DNA segment, or almost the same segment, occurs a plurality (i.e., at least two) of times in a particular DNA sequence or in a particular plurality of DNA sequences. Individual DNA segment size: and/or DNA repeated segment size can vary greatly. For example, in the case of the human genome, each DNA repeated segment is now believed to be typically in the approximate size range of about 5 to about 3,000 bp. Illustratively, a single alphoid DNA sequence may incorporate at least about five different DNA repeated segments. As is known, a chromosome characteristically contains regions which have DNA sequences that contain DNA repeated segments. Small sequential variations in individual segment repeats may possibly occur; see, for example, Waye, J. S. et al., *Molecular and Cellular Biology* 6:3156–3165 (1986).

The term "genome" designates or denotes the complete, single-copy set of genetic instructions for an organism as coded into DNA of the organism. In the practice of the present invention, the particular genome under consideration is typically multi-chromosomal so that such DNA is cellularly distributed among a plurality of individual chromosomes (which number, for example, in man 22 pairs plus a gender associated XX pair or an XY pair).

In the practice of this invention, the genome involved in any given instance is preferably from a primate, and the DNA sequences containing the DNA repeated segments are preferably alphoid or are associated with the centromere of a chromosome type. As used herein, the term "alphoid" or "alpha satellite" in reference to DNA has reference to the complex family of tandemly repeated DNA segments found in primate genomes. Long tandem arrays of alpha satellite DNA based on a monomer repeat length of about 171 base pairs are located principally at the centromeres of primate chromosomes.

The term "chromosome" refers to the heredity-bearing gene carrier of a living cell which is derived from chromatin and which comprises DNA and protein components (especially histones). The conventional internationally recognized individual human genome chromosome numbering identification system is employed herein. The size of an individual chromosome can vary from one type to another with a given multi-chromosomal genome and from one genome to another. In the case of the (preferred) human genome, the entire DNA mass of a given chromosome is usually greater than about 100,000,000 bp. For example, the size of the entire human genome is about $3 \times 10^9$ bp. The largest chromosome, chromosome no. 1, contains about $2.4 \times 10^8$ bp while the smallest chromosome, chromosome no. 22, contains about $5.3 \times 10^7$ bp (Yunis, J. J. in *Science* 191:1268–1270 (1976), and Kavenoff, et al. in *Cold Spring Harbor Symposia on Qualitative Biology* 38:1–8 (1973)).

The term "region" indicates a portion thereof which contains DNA repeated segments that are preferably alphoid or associated with the centromere. The actual physical size or extent of such an individual region can vary greatly. An exact quantification of such a region cannot now be made for all possible regions. Usually, a region is at least large enough to include at least one DNA sequence that (a) incorporates a plurality of copies of at least one DNA repeated segment and that (b) is identifiable and preferably enumeratable optically by fluoroscopic microscopic examination after formation of fluorophore labeled hybrids in such region following an in situ hybridization procedure with a direct label probe or probe composition. Presently available information suggests that a region may contain more than a single such DNA sequence with each such DNA sequence containing one or more DNA repeated segments. Each DNA sequence that occurs in a region may typically contain perhaps from about 70,000 to about 20,000,000 bp, with a present preferred regional DNA sequence size estimate being in the range of about 80,000 to about 225,000 bp, and with a presently most preferred such regional DNA sequence size estimate being in the range of about 100,000 to about 200,000 bp. However, larger and smaller DNA sequences can occur in a single region of a chromosome.

The term "region" is typically and characteristically a chromosome fragment which comprises less DNA mass or size than the entire DNA mass or size of a given chromosome. As is know, not all the DNA of a given chromosome of chromosome region is arranged as DNA sequences containing or comprised of DNA repeated segments. A region, for example, can have a size which encompasses about $2 \times 10^6$ to about $40 \times 10^6$ bp. which size region encompasses, for example, centromeres of the human chromosomes. Such a size is thus a substantial fraction of the size of a single human chromosome. Such a region size is presently preferred as a region size in the practice of this invention although larger and smaller region sizes can be used. A centromeric region of even a small human chromosome is a microscopically visible large portion of the chromosome, and a region comprising DNA repeated segments (not alphoid or centromeric) on the Y chromosome occupies the bulk of the chromosome and is microscopically visible.

In general, the term "region" is not definitive of a particular one (or more) genes because a "region" does not take into specific account the particular coding segments (exons) of an individual gene. Rather, a "region" as used herein in reference to a chromosome is unique to a given chromosome by reason of the particular confirmation of DNA segments therein for present probe composition formation and use purposes.

The term "centromere" refers to a heterochromatic region of the eucaryotic chromosome which is the chromosomal site of attachment of the kinetochore. The centromere divides just before replicated chromosomes separate, and so such holds together the paired chromatids.

The term "gene" designates or denotes to a DNA sequence along a chromosome that codes for a functional product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" or "probe composition" refers to a polynucleotide or a mixture of polynucleotides, such as DNA sequence(s), or DNA segment(s), which has (or have), been chemically combined (i.e., associated) with individual label containing moieties. Each such polynucleotide of a probe is typically single stranded at the time of hybridization to a target.

The term "label" or "label containing moiety" refers in a general sense to a moiety, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (or fluorescent).

Preferably probe compositions made from the chromosomal regional sequences provided herewith contain DNA segments that are chemically bound to label-containing moieties. Each label-containing moiety contains at least one fluorophore (fluorescent) group, and each label-containing moiety is derived from a monofunctional radical-containing, and also fluorophore group-containing, fluorescent starting compound. Such a fluorophore group is covalently bound to a linking group that is itself transaminated as taught herein to DNA segment.

The term "direct label probe" (or "direct label probe composition") designates or denotes a nucleic acid probe whose label after hybrid formation with a target is detectable without further reactive processing of hybrid. Conventionally, a direct label probe incorporates either a fluorophore group or a radioisotope as an individual label moiety.

The term "indirect label probe" (or "indirect label probe composition") designates or denotes a nucleic acid probe whose label after hybrid formation with a target must be further reacted in subsequent processing with one or more reagents to associate therewith one or more moieties that finally result in a detectable entity.

The term "target", "DNA target" or "DNA target region" refers to at least one nucleotide sequence, such as a DNA sequence or a DNA segment, all or a portion of which is complementary to and hybridizable with the nucleotide sequence(s) of a given probe. Each Such sequence or portion is typically being single stranded at the time of hybridization. When the target nucleotide sequences are located only in a single region or fraction of a given chromosome, the term "target region" is sometimes applied. When a given specimen or sample is merely suspected of containing one or more target complementary nucleotide sequences relative to a probe composition, a general term such as "target" or "target composition" is sometimes used herein.

The term "hybrid" refers to the product of a hybridization procedure between a probe and a target. Typically, a hybrid is a molecule that includes a double stranded, helically configured portion comprised of complementarily paired single stranded molecules, such as two DNA molecules, one of which is a target DNA nucleotide sequence, and the other of which is the labeled DNA nucleotide sequence of a probe.

The term "fluorescent" (and equivalent terms) has general reference to the property of a substance (such as a fluorophore) to produce light while it is being acted upon by radiant energy, such as ultraviolet light or x-rays.

The term "fluorescent compound" or "fluorophore group" as used herein generally refers to an organic moiety. A fluorescent compound is capable of reacting, and a fluorophore group may have already reacted, with a linking group.

The term "linking compound" or "linking group" refers to a hydrocarbonaceous moiety. A linking compound is capable of reacting, and a linking group may have already reacted, with a nucleotide (or nucleotide sequence). A linking compound is also capable of reacting, and a linking group may have already reacted with a fluorescent compound.

The term "in situ hybridization" has reference hybridization and preferably detection of a probe to a target that exists within a cytological or histological specimen. As a result of an in situ hybridization procedure, hybrids are produced between a probe (or probe composition) and a target or targets. This term "in situ hybridization" may also be inclusive herein of a hybrid or probe detection procedure which is practiced after hybridization of a probe to a target. A specimen can be adhered as a layer upon a slide surface, and a specimen can, for example, comprise or contain individual chromosomes or chromosomal regions which have been treated to maintain their morphology under, for example, denaturing conditions and conditions such as typically exist during flow cytomeric analyses subsequent to hybridization of a probe to a target. The term "in situ hybridization" may include use of a counterstain. In the case of the inventive fluorophore labeled probes or probe compositions, the detection method can involve fluorescence microscopy, flow cytometry, and the like.

The term "hybridizing conditions" as has general reference to the combinations of conditions that are employable in a given hybridization procedure to produce hybrids, such conditions typically involving controlled temperature, liquid phase, and contacting between a probe (or probe composition) and a target composition. Conveniently and preferably, at least one denaturation step precedes a step wherein a probe or probe composition is contacted to a target. Alternatively, a probe can be contacted with a specimen comprising a DNA target region and both subjected to denaturing conditions together as described by Bhatt, et al in *Nucleic Acids Research* 16:3951– 3961. The presence of an agent or agents which in effect lower the temperature required for denaturation and subsequent hybridization between probe (or probe composition) and target is generally desirable, and a presently most preferred such agent is formamide. Using, for example, about a 50:50 weight ratio mixture of water and formamide, an illustrative temperature for thermal denaturation is in the range of about 35° to about 70° C. applied for times that are illustratively in the range of about 1 to about 10 minutes, and an illustrative temperature for contacting and hybridization between probe (or probe composition) and target is in the range of about 35° to about 55° C. applied for times that are illustratively in the range of about 1 to about 16 hours. Other hybridizing conditions can be employed. The ratio of numbers of probes to number to target sequences or segments can vary widely, but generally the higher this ratio, the higher the probability of hybrid formation under hybridizing conditions within limits.

The term "lower" as used herein in reference to an individual compound, group or radical means that such compound, group or radical contains less than 6 carbon atoms.

The term "clone", "cloning" or equivalent refers to the process wherein a particular nucleotide segment or sequence is inserted into an appropriate vector, the vector is then transported into a host cell, and the vector within the host cell is then caused to reproduce itself in a culturing process, thereby producing numerous copies of each vector and the respective nucleotide sequence that it carries. Cloning results in the formation of a colony or clone (i.e., group) of identical host cells wherein each contains one or more copies of a vector incorporating a particular nucleotide segment or sequence. The nucleotide segment or sequence is now said to be "cloned", and the product nucleotide segments or sequences can be called "clones."

The term "library" is used herein in its conventional sense, to refer to a set of cloned DNA fragments which together represent an entire genome or a specified fragment thereof, such as a single chromosome. Various libraries are known to the prior art and are available from various repositories, and techniques for genome and genome fragment preparation, and for cloning libraries therefrom, are well known. A present procedural preference is to fragment a selected one chromosome that was separated by flow sorting or the like. Fragmentation prior to cloning is preferably achieved by digestion with restriction endonucleases or the like. This procedure produces fragment ends which are particularly amenable to insertion into vectors. However, those skilled in the art will appreciate that any conventional or convenient technique for fragmentation can be used. The fragments are then conventionally cloned to produce a chromosome library.

(B) Starting Materials (1) The Starting Oligonucleotides

Conveniently and preferably, at least one oligonucleotide is used in the practice of making a regionally specific cloned DNA sequence of this invention. Each such oligonucleotide is complementary to a location in a DNA sequence which occurs in a preselected region of a chromosome and which is located approximately between adjacent DNA repeated segments that occur in such preselected region. While only a single oligonucleotide is sufficient, an oligonucleotide mixture of at least two structurally differing short (i.e., oligomeric) common DNA repeated segments which bound (i.e. terminate) DNA repeated segments specific to a preselected region of a given chromosome is presently preferred.

For individual human chromosomes, the structures of such degenerate (i.e. synthesizable) commonly occurring oligonucleotide segments which occur in such a DNA sequence are generally known, as are methods for their identification. See, for example, Koch J. E., et al., *Chromosoma* 98:259–265 (1989). Typically, suitable synthesized oligonucleotides complementary to such DNA repeated segments can contain about 17 to about 50 bp, preferably about 15 to about 30 bp, but larger and smaller oligonucleotides can be prepared and used, if desired.

The known identification methods can be readily used for identifying the DNA repeated segments that are present in a given region of a chromosome, such as alphoid DNA in the centromere region, in any multi-chromosomal genome, as those skilled in the art will readily appreciate. From such an identification, desired complementary oligonucleotide segments can be derived and synthesized for a given chromosome. The complete nucleotide structure of the DNA sequence wherein such DNA repeated segments naturally occur need not be known and, indeed, usually is not known, as those skilled in the art will appreciate.

Once derived (i.e., identified), the oligonucleotides are readily synthesized using conventional, commercially available nucleotide sequence generating apparatus and methods. See, for example, M. H. Caruthers, in Science, 281–285 (1985). One presently preferred DNA synthesizing machine is the Applied Biosystems Model 38D B DNA Synthesizer available commercially from Applied Biosystems (Foster City, Calif.). Such a machine was employed for synthesis of starting oligonucleotides employed in the examples described herein.

(2) The Starting Chromosomal Template DNA

The starting chromosomal DNA template sequences used in the practice of this invention comprise DNA from a preselected whole chromosome (of a multi-chromosomal genome) wherein a preselected region occurs. This template DNA is typically in the form of a plurality of DNA sequences which taken together contain a multiplicity of DNA segments that individually occur at various locations in and throughout such chromosome and that are reasonably representative of DNA occurring in the preselected chromosome. Although in its naturally occurring state, such a starting DNA sequences may typically have a size much greater than about one million base pairs, at the time of availability for use as a starting material in the practice of this invention, such sequence may already be somewhat fragmented, depending upon such factors as the methods used in separation, isolation and the like. Preferably, such chromosome is from the human genome.

For purposes of preparing a cloned DNA sequence of this invention, the starting chromosomal DNA sequence(s) can be obtained by various techniques. Thus, such can be derived or obtained from (a) DNA of a preselected chromosome that is separated by flow sorting or the like and purified from component intracellular material of an organism; (b) a library of a preselected chromosome; and (c) an interspecies hybrid which incorporates DNA from a preselected chromosome. A presently preferred stating chromosomal DNA is a chromosome library that has been prepared by standard methods and is available from traditional sources known to those in the art, such as the American Type Culture Collection (ATCC) or other repositories of human or other cloned genetic material. While a large number of specific chromosome libraries are available from the ATCC, representative libraries are shown in Table I below:

TABLE I

HUMAN CHROMOSOME LIBRARIES

| Human Chromosome Library | ATCC No. | Human Chromosome Library | ATCC No. |
|---|---|---|---|
| 1 | 57738 | 13 | 57757 |
| 1 | 57753 | 14 | 57739 |
| 1 | 57754 | 14 | 57706 |
| 2 | 57716 | 14/15 | 57707 |
| 2 | 57744 | 15 | 57729 |
| 3 | 57717 | 15 | 57740 |
| 3 | 57748 | 15 | 57737 |
| 3 | 57751 | 16 | 57765 |
| 4 | 57719 | 16 | 57730 |
| 4 | 57718 | 16 | 57749 |
| 4 | 57700 | 16 | 57758 |
| 4 | 57745 | 17 | 57741 |
| 5 | 57720 | 17 | 57759 |
| 5 | 57746 | 18 | 57742 |
| 6 | 57721 | 18 | 57710 |
| 6 | 57701 | 19 | 57731 |
| 7 | 57722 | 19 | 57766 |
| 7 | 57755 | 19 | 57711 |
| 8 | 57723 | 20 | 57732 |
| 8 | 57707 | 20 | 57712 |
| 9 | 57724 | 21 | 57743 |
| 9 | 57705 | 21 | 57713 |
| 10 | 57725 | 22 | 57733 |
| 10 | 57736 | 22 | 57714 |
| 11 | 57726 | X | 57750 |
| 11 | 57704 | X | 57734 |
| 12 | 57727 | X | 57752 |
| 12 | 57736 | X | 57747 |
| 13 | 57728 | Y | 57735 |
| 13 | 57705 | Y | 57715 |

The ATCC deposits of Table I are available from the American Type Culture Collection, 12301 Parklawn Drive, Rockville, Md.

Examples of prior art teachings illustrating the preparation of suitable starting preselected chromosomal template sequences for making region specific DNA sequences of this invention include (but are not limited to):

1. Physically separated chromosomes or libraries derived from same, as in M. A. Van Dilla, et al. in *Bio/Technology* 4:537–552 (1986).

2. A microdissected chromosome, fragment of a chromosome or cloned library derived from same, as in Ludecke, H. J., et al. in *Nature* 338:348–350 (1989).

3. Single human chromosomes or fragments thereof, which are propagated in rodent cell lines. A method for the generation of human, mono-chromosomal hybrid lines is described in: Carlock. L. R., et al. in *Somatic Cell Mol. Gent.* 12:163–174 (1986).

The starting chromosomal DNA typically contains about 18 to about 25 mole percent deoxycytidine nucleotides based on the total number of deoxynucleotides present therein. Typically, the starting template chromosomal DNA of the preselected single chromosome wherein the preselected region exists displays a wide variation in molecular size, for example, the sizes can be in the range of about 150 to about 20,000,000 bp.

(3) The Starting Linking Compound

A starting linking compound employed in the practice of this invention is a difunctional organic compound, that is, such contains two substituent functional (i.e., reactive) substituents per starting linking compound molecule.

At least one of such functional substituents per linking compound molecule is reactive with deoxycytidine nucleotides in a polynucleotide under bisulfite catalyzed aqueous transamination conditions (such as provided herein, for example). Examples of such substituents include alkyl amino (primary and secondary) hydrazide, semicarbazido, thiosemicarbazido, and the like. Amino groups are presently most preferred.

When the amino group is secondary, the secondary substituent is preferably a lower alkyl group, but other non-blocking such secondary substituents can be used, if desired.

The second of other of such two functional substituents per linking compound molecule is reactive with a third functional substituent which is itself incorporated into a starting fluorescent compound (as herein described). Such second functional substituent can itself be either blocked or unblocked. When the second substituent is unblocked, then it is substantially non-reactive with other substances that are present in the transamination medium (especially polynucleotides) during transamination. When the second substituent is blocked then it is substantially non-reactive with the other substances that are present in the transamination medium (especially polynucleotides) during transamination.

Examples of suitable unblocked second functional substituent group include amino, carboxyl, phosphate, sulfonate, hydroxyl, hydrazido, semicarbazido, thiosemicarbazido and the like. Presently, most preferred unblocked second functional substituent include amino (primary or secondary) and carboxyl groups.

The carboxyl group preferably is either in the salt form or in the acid form, but can sometimes be in the ester form. When in the salt form, presently preferred cations are alkali metals, such as sodium and potassium.

Examples of suitable blocked second functional substitutent group include blocked sulfonate, blocked phosphate, blocked sulfhydryl, and the like.

Examples of suitable blocking substituents include lower alkyl groups such as methyl, ethyl, propyl, etc.

The first and the second functional substituents are interconnected together through a linker (or linking) moiety. This linking moiety can have any convenient structure but such is non-reactive with other substances that are present in the transamination medium during transamination. A present preference is that the linking moiety be a hydrocarbonaceous divalent group which is acyclic or cyclical and which can optionally incorporate other atoms.

The two functional substituents present in such a difunctional linking compound can be respective substituents of the linking moiety. Such substituents can be on adjacent carbon atoms relative to each other, or they can be spaced from one another in a linking compound molecule by a plurality of intervening interconnected atoms (preferably carbon atoms). Preferably these functional groups are in an alpha, omega relationship to one another (that is, each is at a different opposite end region) in a given linking compound molecule.

Thus, the two functional radicals in a linking compound are each bonded to an organic linking group moiety which is either entirely hydrocarbonaceous (that is, composed only of carbon and hydrogen atoms), or is comprised of carbon and hydrogen atoms plus at least one additional atom or group which contains at least one atom selected from the group consisting of oxygen, sulfur, nitrogen, phosphorous, or the like. Preferably such additional atom(s) are so associated with such organic moiety as to be substantially less reactive than either one of such above indicated two functional radicals that are present in a given starting linking compound. Hydrocarbonaceous organic moieties that are saturated aliphatic are presently preferred, and more preferably such moiety is a divalent alkylene radical containing from 2 through 12 carbon atoms, inclusive. However, if desired, such a saturated aliphatic radical can incorporate either at least one ether group (—O—) or at least one thio-ether group (—S—), but it is presently more preferred that only one of such ether or thio ether groups be present. It is presently preferred that a linking compound incorporates an organic radical that contains at least two and not more than about a total of about 20 carbon atoms, although more carbon atoms per molecule can be present, if desired.

Presently preferred are linking compounds in which each of such functional radicals is an amino radical. Both acyclic and cyclic diamino compounds can be used.

Examples of suitable aliphatic primary diamines include alkylene primary amines wherein the alkylene group is propylene, butylene, pentylene, hexylene, nonylene, and the like.

Examples of suitable aliphatic secondary diamines include $CH_3NH(CH_2)_2NH_2$, $CH_3NH(CH_2)_2NHCH_3$, and the like.

Diamino compounds incorporating hydroxylated hydrocarbons can be used. Examples of acyclic such compounds include 1,3-diamino-2-hydroxypropane; 1,4-diamino- 2,3 dihydroxybutane; 1,5-diamino-2,3,4-trihydroxypentane; 1,6-diamino-1,6-dideoxy-D-mannitol (or D-glucitol or D-galactitol), 1,6-diamino-2,3,4,5-tetrahydroxy hexane, and the like.

Examples of suitable polyhydroxylated cyclic dimensions include cis or trans cyclic diamino compounds where the diamines are constrained in a ring, such as 1,4-diamino-2,3,5,6-tetrahydroxy cyclohexane, cis and trans 1,2-diaminocyclohexane, cis and trans 1,2-diaminocyclopentane, and hydroxylated derivatives thereof, such as 1,2-diamino- 3,4, 5,6-tetrahydroxycyclohexane, 1,2-diamino-3,4,5-trihydroxy cyclopentane, 3,6-diamino-3,6-dideoxy-derivatives of myo-inositol, such as

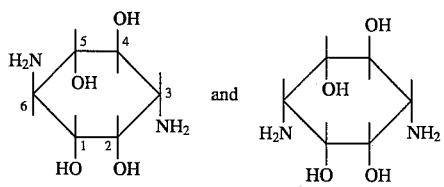

and the like.

Examples of suitable heterocyclic diamines include piperazine, N,N'-bis (3-aminopropyl) piperazine, derivatives thereof, and the like.

Examples of suitable ether-group containing diamines include 3-oxo-1,5-pentanediamine, 3,6-dioxo-1,8-diaminooctane, and the like.

Examples of suitable linking compounds containing both an amino radical and a carboxyl radical include amino acids, such as sarcosine (N-methylglycine), and alpha amino acids, such as glycine, alanine, glutaric acid, aspartic acid, proline, pipecolinic acid (piperidine-2-carboxylic acid), isopipecolinic acid (piperidine-4-carboxylic acid), glucosaminic acid and derivatives thereof, and the like.

Examples of alpha, omega aminocarboxylic acids (in addition to the above identified amino acids) include 4-aminobutyric acid, 6-aminohexanoic acid, 8-aminooctanoic acid, and the like.

Examples of phosphorous containing difunctional linking compounds include alpha, omega aminoalkyl phosphoric acid, monoesters, such as O-(2-aminoethyl) phosphate disodium salt and the like.

Examples of suitable sulfur containing difunctional linking compounds include alpha, omega aminoalkyl sulfonic acids, such as taurine (2-aminoethyl sulfonic acid) and the like.

One presently more preferred class of difunctional linking compounds is represented by the following generic formula:

$$\begin{array}{c} R_1 \\ | \\ H-N-R-X-H \end{array} \quad (1)$$

wherein:

X is a divalent radical selected from the class consisting of:

wherein:

R is an alkylene radical containing from 2 through 12 carbon atoms inclusive or carbocyclic ring hydroxylated car carboci, and $R_1$ and $R_2$ are each independently selected from the class consisting of hydrogen and lower alkyl.

Preferably, in Formula (1), R contains not more than 7 carbon atoms, X is $R_1$ and $R_2$ are each hydrogen, and X is

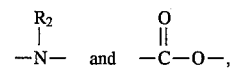

and $R_1$ and $R_2$ are each hydrogen, and R contains less than 7 carbon atoms.

Mixtures of different linking compounds can be used, such as linking compounds containing a mixture of mono and/or diamines, but such mixtures are not preferred because associated problems in transamination control and usage.

Diamines which are characterized by having a large proportion thereof that exists as a free unprotonated species at pH values of about 7 appear to enhance the present transamination reaction. Ethylene diamine (pK of about 7.6) is presently most preferred for use as the reactive difunctional amine because of this property.

When, for example, such a linking compound is bonded to a DNA sequence using a transamination reaction, as hereinbelow described, the transamination reaction is carried out so that an amino radical in the linking compound bonds to the sequence or segment. Then, in the resulting linking group, one functional group remains free to undergo further reaction. Thus, when the second functional radical is an amino radical, such radical remains free thereafter to undergo further reaction with the fluorescent compound, as hereinbelow described. When the second functional radical is a carboxyl radical, such radical remains free thereafter to undergo such a further reaction with the fluorescent compound, as hereinbelow described.

(C) Production of Cloned Regional Chromosomal Sequence

The present invention provides a process for producing a cloned DNA sequence that (a) is complementary to a DNA sequence which occurs in one selected region of one selected chromosome that is preferably of a multi-chromosomal genome, and also that (b) incorporates a plurality of copies of at least one DNA repeated segment which occurs in such one selected region.

Briefly, this process involves, as a first step, synthesizing at least one starting oligonucleotide (as above described). Each such oligonucleotide contains a nucleotide sequence that is complementary to at least one DNA repeated segment existing in such one region. Next, one uses such starting oligonucleotide(s) to enzymatically amplify starting chromosomal DNA of the whole chromosome wherein the selected region occurs, such starting chromosomal DNA being as above described. The oligonucleotide(s) is/are used as the primer composition and whole chromosomal DNA is used as the template. There is thus produced an amplified class of copies of DNA repeated segments existing in such one region. Then, such class of amplified DNA repeated segment copies, a group of separated and sampled copies thereof are produced. These sampled separated copies are individually labeled and hybridized with respective specimens of a target comprised of component DNA which is representative of the whole genome so as to produce hybrids. From such hybrids, a DNA sequence which occurs only in the one selected region is identified and selected and copies thereof are cultured and extracted for use.

An inventive cloned DNA sequence that is prepared as described herein is complementary to (that is, is substantially an exact and complete replicate of) a DNA sequence which occurs in one selected region of one chromosome of a particular genome that is typically multi-chromosomal (i.e., is eukaryotic in biological origin). Also, each such cloned DNA sequence contains incorporated thereinto at least one, and preferably a plurality (that is, at least two) DNA repeated segments and more preferably at least 5 different DNA repeated segments. The size of (that is, the number of nucleotides or base pairs in) such a cloned DNA sequence, and the individual DNA repeated segment(s) therein, and other variables, such as the segment nucleotide sequences, the segment arrangement in each sequence, and the number of DNA repeated segments in the DNA sequence, and the like, are typically not known; however, such information need not be known for purposes of practicing the present invention. A single such cloned DNA sequence can contain a nucleotide sequence of at least about 1000 bp and usually not more than about 100,000 bp. Illustratively, in a single alphoid DNA sequence that can occur in a single region of a chromosome may contain from about 20,000 bp to many hundreds of thousands of base pairs. More than one DNA sequence can be present in a selected chromosome region.

More specifically, to produce a cloned DNA sequence of this invention, one preliminarily synthesizes at least one commonly occurring oligonucleotide (as above indicated) that is complementary to a portion of at least one DNA repeated segment existing in at least one DNA sequence of one selected region of one selected chromosome. The human genome is presently preferred, and a chromosomal region containing a plurality of alphoid DNA repeated segments is presently preferred.

Although only a single starting oligonucleotide segment can be used in the practice of this invention as a primer, in the enzymatic amplification, a present preference is to employ a mixture of oligonucleotides which contain at least two, more preferably at least five, but generally not more than about 64 different oligonucleotides. Various numbers of oligonucleotides can be used in such a starting oligonucleotide mixture. The weight ratio of one to another of such individual different oligonucleotides in a given oligonucleotide mixture is typically about equal owing to the known methods by which they are synthesized. In the absence of prior knowledge of the sequence of the DNA repeated segments in any given selected region, there is at present no known way to estimate accurately how many copies of the complement of any given oligonucleotide will be present in any given sequence or chromosome region. The general requirement for enzymatic amplification is that primers which are sufficiently complementary to the target template hybridize under the annealing conditions used in the reaction be present in sufficient amount to allow the synthesis of a sufficiently large number of copies of the template to be useful, thereby to achieve reproduction and detectable amplification of a template sequence.

When structural differences occur because of positional degeneracies in the starting DNA sequences, then a most preferred practice made is to use a primer set for one strand which contains about 8 different oligonucleotides and a primer set for the other strand which contains about 12 different oligonucleotides. Alphoid DNA repeated segments are generally preferred. Thus, presently most preferred starting oligonucleotides are specifically complementary to DNA repeated segments in the alpha satellite DNA repeated segment region of the centromere of a particular selected chromosome of an entire multi-chromosomal genome, most preferably the human genome.

For use in the practice of this invention, it is presently convenient and preferred to prepare initially one or more such oligonucleotides as an aqueous dispersion or composition wherein the concentration of oligonucleotide(s) is consistent with the procedure being used for executing a DNA enzymatic amplification reaction, as those skilled in the art will appreciate.

Such a starting oligonucleotide composition is used as the primer composition in an enzymatic DNA amplification procedure wherein the template is a DNA composition representative of the one entire selected chromosome wherein the selected region occurs. The DNA template is selected and prepared from the selected genome. Thus, for example, such a chromosomal template composition can comprise and be based upon one of the following: (a) the one chromosome, which can be isolated from the genome by flow sorting or the like, (b) DNA fragments which taken together comprise the one chromosome, which fragments can be prepared mechanically (i.e., sonication or the like) or enzymatically or (c) a library of the one chromosome which library can be prepared by cloning a chromosome's DNA fragments. The starting template composition is preferably in the form of an aqueous dispersion wherein the template DNA concentration and condition is likewise consistent with the particular procedure being used for executing an enzymatic amplification procedure, as those skilled in the art will appreciate.

A present preference is to employ as the template a chromosome library wherein the chromosomal DNA fragments are in the size range of about 150 to about 600,000 bp, and more preferably in the range of about 150 to about 35,000 bp, and most preferably about 150 bp to about 10,000 bp. Such DNA fragment size ranges can be used with various members of the vector types now commercially available for propagation in either bacterial or fungal hosts, as those skilled in the art will appreciate.

In the enzymatic amplification procedure, primers are used as "building blocks" for producing DNA repeated segments which are exact copies of DNA repeated segments found in template nucleotide sequence areas, such areas being complementary to the primer sequences. The DNA enzymatic amplification procedure can be carried out by using, for example, the well known so-called polymerase chain reaction procedure (PCR). For example, suitable commercially available PCR apparatus and methods are available from Perkin Elmer-Cetus (Norwalk, Conn.), such as the Perkins Elmer-Cetus DNA Thermal Cycler and operating instructions provided therewith. The reagents employed can be in the form of the so-called Perkin Elmer-Cetus "Gene Amp" kit. Such equipment and reagents were employed in the examples described hereinbelow. See also K. B. Mullis, et al. in *Methods in Enzymology* 155:335–350 (1987).

A present preference is to conduct the DNA enzymatic amplification procedure automatically or semi-automatically and to employ in a given procedure at least about 20 cycles of amplification with each cycle having a time duration in the range of about 2 to about 6 minutes. Preferably, the final cycle is somewhat prolonged relative to the preceding cycles. The amplified product is characteristically a mixture (or class) of DNA polynucleotides containing copies of DNA repeated segments present mainly in the selected one region of one chromosome. The selected region is thus in effect determined by the location in the chromosome where the oligonucleotides mainly occur.

Such a resulting enzymatically amplified class of copies of DNA repeated segments of the one chromosome are conveniently conventionally separated, for example, by extraction with a solvent mixture, such as phenol and chloroform, or the like, followed by precipitation with ethanol, or the like. The mixture can be fragmented. A product mixture is conveniently and preferably suspended in a compatible sterile aqueous carrier medium at a concentration which is preferably convenient for the subsequent usage thereof as herein described. In such a product mixture composition, the DNA segments can typically and preferably each contain about 170 to about 3000 bp. each, although larger and smaller segments can be employed.

Next, a locating procedure is undertaken to select a group (i.e., a plurality) of individual DNA segments which are characteristically found in the one selected region of the selected one chromosome, and to sample same. This locating procedure is carried out using the enzymatically amplified class of DNA segments. The procedure utilizes a class of clone colonies whose host cell individual colony members incorporate at least individual vector DNA repeated segments of the one selected chromosome. Those skilled in the art will appreciate that various locating procedures can be used.

In the presently employed preferred locating procedures, the individual member clone colonies of a class of clone colonies are maintained discretely (i.e., separately) relative to each other, preferably in flattened surface portions of a solidified cell culture medium. Each individual colony thus contains a plurality of substantially identical host cells.

Because such an enzymatically amplified product is itself a mixture of various different nucleotide sequences, and because each vector typically incorporates only a single nucleotide sequence, a group of vectors that incorporate such an enzymatically amplified product is itself a mixture or class. However, the vectors in the cells of each individual colony are identical to one another. The cloning processes utilized in the selection procedures employed in this invention are adapted to enhance the capacity to achieve the desired selection of individual vector DNA sequences.

Thus, in one of the presently preferred locating procedures, the enzymatically amplified class of copies of DNA repeated segments is cloned. The cloning procedure employed utilizes the steps of:

a) inserting individual members of the enzymatically amplified DNA repeated segments class into respective individual vectors, b) transporting the vectors into host cells at a rate of about one vector per host cell, c) seeding the so transported host cells upon a solidified cell colony culture medium, and d) culturing the so seeded host cells to produce a host cell class of medium surface distributed separate cloned colonies, each colony containing mainly individual vector DNA repeated segments incorporated therein.

To prepare the enzymatically amplified class of DNA segments for cloning, the member DNA segments can be preliminarily digested with restriction enzymes to produce nucleotide sequence fragments which can be incorporated into individual vectors. A present preference is to employ segment fragments having a size in the range of about 170 to about 3000 bp, and most preferably about 1500 to about 3000 bp, although larger and smaller sizes can be used. The choice of fragment size in any given instance is influenced by many variables, such as the vector employed, the maximum size of the products obtained, the restriction sites available for insertion of the enzymatically amplified product, and the like, as those skilled in the art will appreciate.

If desired, one can employ, for example, a cloning procedure such as the procedure advertised by Invitrogen Corporation of San Diego, Calif. and termed "TA cloning" which allows direct cloning of enzymatically amplified nucleic acids from genomic DNA without an intervening processing with restriction enzymes or the like (see advertisement of Invitrogen Corp. in *Science* 251, 609 (Feb. 8, 1991).

As cloning vectors, it is presently preferred to use plasmids, such as the plasmids identified by the identification codes pUC18, pUC19, pBS1, pGEM3, and the like, all of which are available from various commercial sources. The inserting of individual members of the enzymatically amplified class of DNA repeats into respective individual vectors, and the transforming of such vectors into host cells, is conventionally accomplished.

A presently preferred host cell is a bacterium, and a presently particularly preferred bacterium is *E. coli*, for reasons of convenience, availability and reliability. Seeding of transported host cells is conventionally accomplished, and the solidified cell colony culture medium can be conventional. Methods for the preparation and the transformation of competent *E. coli* host cells, and the subsequent agar plating and culturing steps required to isolate cell populations transformed with a single type of recombinant plasmid or filamentous phage are described, for example, in "Molecular Cloning: A Laboratory Manual," 2nd ed. pp. 1.35–1.84 and 4.21–4.36 by J. Sambrook, et al. published by Cold Spring Harbor Laboratory Press, Cold Spring Harbor, N.Y. (1989).

There is thus produced a host cell class of colonies which are distributed over surface portions of the solid-like culture medium and whose colony members taken together contain vector DNA sequences identical to those of the members of the class of enzymatically amplified DNA sequences. However, the host cells of each member colony incorporate mainly only one particular vector DNA sequence which is statistically structurally different from the vector DNA sequences contained in other colonies of the colony class.

The colony class is then sampled. A small representative sample of host cells is taken from each of a number of colonies, and each such cell sample is then individually cultured (i.e., fermented). A conventional colony random sampling technique is employable. The culturing procedure including the culture medium can each be similar to those described in the above referenced Sambrook et al. work.

Thus, there is provided a plurality of selected and separately multiplied (i.e., cloned) individual vector DNA repeated segments.

In the second of the presently preferred selection procedures, the enzymatically amplified class of DNA repeated segments is labeled so as to produce a probe composition. For example, the labeling can be accomplished with, for example, radioisotopes, biotin, hapten antigens, or the like, so as to produce a probe composition comprised of a mixture of labeled DNA sequences.

Such labeling can be achieved by any convenient procedure, including nick-translation, random oligonucleotide priming, and like methods known to the prior art. The presently preferred method utilized in the practice of this invention involves incorporating a direct label into the enzymatically amplified class of DNA repeated segments by incorporation of alpha $^{32}$p dCTP during the enzymatic amplification procedure. Thus, one can add, for example, about 100 microcuries (μCi) of alpha $^{32}$p dCTP (deoxycytidine 5' triphosphate, tetra-triethylammonium salt, [alpha -$^{32}$p] to a conventional Perkin Elmer-Cetus PCR reaction mixture, such as is available commercially and as described in literature accompanying the PCR apparatus supplied by this concern. Substantially no interference with sequence complementary characteristics should occur as a result of labeling or the labeling process, as those skilled in the art will appreciate.

As part of the present locating or selection procedure, one obtains or prepares a colonized genome library of the genome which incorporates the one selected chromosome. The preparation procedure employed utilizes the steps of:

a) fragmenting the genome into a class of DNA sequences and/or segments; and b) cloning the fragments to form a library of the genome. The cloning procedure can involve the same steps and conditions as above identified in reference to the cloning procedure used for the enzymatically amplified class of DNA repeated segments, or otherwise, if desired.

The colonized genome library is converted into separated patches of single stranded DNA sequences (or fragments) that are arrayed (that is, distributed over) a support substrate, such as nitrocellulose, or the like. A conventional arraying procedure can be employed. Thus, a master copy of the library array is formed. Then, the following further procedural preferred steps are preferably utilized:

a) replicating the master copy library array of colonized cells upon a support substrate; and b) processing the DNA copies in the replicated library array.

The replicate copy processing comprises lysing host cells, denaturing the DNA in each colony area, and fixing the DNA to the supporting matrix.

Conventional support substrates in sheet form can be used, and presently most preferred support substrate sheets are comprised of nitrocellulose, derivatized nylon or an equivalent material. For example, DNA from E. coli colonies growing on nutrient agar plates can be lysed, denatured and affixed to nitrocellulose membranes utilizing the method described by Sambrook et al. in the above-cited work at pp. 1.90–1.104.

Next, in the present locating procedure, the probe composition is hybridized under hybridizing conditions with a target comprising the DNA in each of the so processed areas of the so replicated and processed library. Any convenient protocol can be employed. For example, the screening protocol can be similar to that employed in the so called colony hybridization procedures known to the prior art; see, for example, the procedures described by Sambrook et al. in their above cited work at pp. 1.90–1.104 and P. J. Mason et al. at pages 119–121 of "Nucleic Acid Hybridization" edited by B. D. Hames and S. J. Higgins, published by IRL Press first in 1985.

The resulting hybridized DNA and hybrids are then examined. From the resulting hybrids, particular DNA repeated segments that exist in the replicated and processed library are identified. These repeated segments characteristically occur mainly only in the selected one region of the one chromosome. The identification is based on those library target DNA fragments which contain or comprise DNA segments that are complementary to DNA segments in the probe composition. The examination identification procedure utilizes:

a) autoradiographing with X-ray film the so hybridized substrate, thereby to produce individual darkened areas on the resulting so exposed and developed film which correspond to the locations of hybrids;

b) first identifying the particular separated DNA fragments in the replicated array which are associated with individual darkened areas on the film; and then c) secondly identifying those host cell colonies within the master copy of the colonized genome library which incorporate the particular respective so first identified DNA fragments.

For example, the first and second identifying can be accomplished by overlaying the so exposed and developed film over the master copy.

The examination and identification procedure preferably employs conventional, commercially available X-ray film which is initially laid over and suitably exposed to the so-hybridized replicate substrate. Various exposure conditions can be employed, as those skilled in the art appreciate.

After host cell colony members which contain complementary DNA repeated segments are thus identified, a suitable sample of host cells is recovered from each so identified colony.

Instead of employing a library derived from an entire genome that is produced for hybridization using the probe composition, one can employ, if desired, only a specific portion of such genome which specific portion is inclusive of the one selected starting chromosome. For example, in the case of the human genome, one can employ a genome specific portion that is comprised of flow sorted chromosomes, chromosomal DNA from inter-species hybrids, or the like.

For an illustration, the specific portion can be a single human chromosome that has been separated from the human genome by flow sorting (that is, the same chromosome type that was initially selected). This chromosome is then fragmented and the fragments are cloned into a library. The chromosome library is then arrayed. Then, the matrix is employed as a target complex for hybridizing under hybridization conditions with the probe composition.

Each such individual so sampled and recovered clone is then cultured. Conveniently, the culturing procedure and the culture medium can be similar to those employed for culturing sampled clones.

Individual clone cell colonies produced in the culture (fermentation) step of box 18 are each subjected to a plasmid extraction procedure which is conveniently conventional and which can be, for example, as described by Sambrook et al. in their above cited work at pp. 125–128. The plasmid DNA thus recovered from each clone colony is then labeled so as to convert each individual extracted plasmid DNA material into a separate probe or probe composition.

As a matter of procedural preference, it is presently preferred that the label moieties used in these probe compositions be readily introduced by incorporation using enzymatic amplification. Thus, for example, indirect labels of biotin derivatized nucleotides are presently preferred. However, if desired, other hapten derivatized nucleotides can be employed. In general, any suitable and convenient procedure known to the prior art can be employed to accomplish such labeling.

Another presently preferred labeling procedure is that which is hereinbelow described in the "Probe Production" section and utilizes fluorophore direct labels.

Preferably, the number of direct or indirect label moieties employed per individual DNA sequence here is in the range of about 5 to about 25 weight percent. (based on total probe composition weight), although this number can be smaller or larger, if desired. Substantially no interference with sequence complementary characteristics should occur as a result of any such labeling. Preferably each probe composition and the sequences thereof are substantially identically labeled using the same labeling procedure relative to others of a class of such probe compositions.

A genomic DNA target composition is prepared which is representative of the entire genome which includes the one selected chromosome. The target composition comprises one of the following:

a) the entire whole multi-chromosomal genome of which the one chromosome of the selected region is one component;

b) DNA fragments which taken together comprise the DNA of the entire genome;

c) at least one fragment or portion of the genome which includes the one chromosome or sequence fragments which taken together comprise the one chromosome;

d) a library derived from the entire genome; or e) a library derived from at least one fragment (or portion) of the genome which fragment includes the one chromosome.

It is presently much preferred to employ (a) (above) as the target composition for reasons associated with ease of observation, characterization and accurate source identification of the hybrids produced therewith.

Each of the probe compositions is then hybridized under hybridization conditions with a sample of the target composition.

For example, by binding fluorescently labeled avidin to the hybridized biotin derivatized probes, one can observe hybrids directly, and by microscopic examination under a microscope equipped for fluorescent evaluation, determine where along a given chromosome structure hybridization has occurred. Knowledge of such location is desirable for purposes of establishing the character of the DNA sequence in the particular probe under evaluation and whether that sequence is complementary to a DNA sequence in the selected region of the one chromosome.

While such a hybridization procedure can be carried out by any convenient technique, it is presently preferred to employ an in situ-type of hybridization procedure. A presently preferred in situ hybridization procedure is described by D. Pinkel, et al. in *Proc. Natl. Acad. Sci. USA* 85:9138–9142 (1988), omitting the RNAse treatment, the Proteinase K treatment and the formaldehyde fixation.

Thus, the target composition is conveniently deposited as a specimen layer upon a central portion of one face of a conventional glass microscope slide. Slide preparation procedures well known to the art can be employed; for example, suitable procedures are described by J. M. Trent, et al. in *Methods in Enzymology* 151:267–279 (1987).

Individual target composition slide layer characteristics can, of course, vary greatly. It is convenient and presently preferred to employ a slide target area wherein the cell nuclei and metaphases are well dispersed. Typically, a slide surface area of about 400 mm$^2$ is utilized, although slide specimen areas of differing size characteristics can be used. Each target layer or area is preferably substantially identical to the other layers concurrently being used in a given hybridization procedure for evaluation of all probe compositions of a given probe composition class.

Also, and preferably, each individual probe composition should be evaluated using more than one individual deposited slide layer to reduce errors and to increase the reliability of results. A present preference is to evaluate each probe composition against two layers.

Next, an examination and identification procedure of all hybrids is carried out to identify which probe compositions are complementary to target DNA sequences that are within the selected chromosomal region. Thus, from the hybrids so produced, at least one single DNA sequence of a probe composition is identified which is complementary to at least one DNA repeated segment and which exists in the selected region. Preferably only one DNA sequence is selected.

The number of fluorophore radicals at a single optical point source required for visualization varies enormously based mainly on four characteristics: 1. The absorbance and quantum yield of the fluorophore employed. The various fluorophore radicals have large differences in both absorbance and yield. 2. The strength of excitation illumination. Many lamps of varying overall power and intensity at a given wavelength are commonly used. The efficiency of the optical train which delivers the light to the sample varies widely over the different microscope brands and models. 3. The efficiency with which emitted light is collected and delivered to the viewer. Again, the quality of the optical train used to produce the image which is viewed varies widely over the different microscope brands and models. 4. Sensitivity of the observer. The average human visual response to the various colors differs across the spectrum, falling off rather precipitously at the lower and higher wavelengths. The viewer may or may not have access to electronic imaging equipment which can greatly enhance his sensitivity of detection. For all of these reasons, there is now believed to be no satisfactory way of providing precise or meaningful quantitative data on the relationship between the number of fluorophores present at a site and the ability of a viewer to see those fluorophores. It is presently preferred to use an empirical route in evaluating signal strength. Thus, reagents can be tested by a number of viewers who each evaluate perceived signal strength.

Indirect labeling for this sequence selection step is presently preferred because the conditions to do this labeling and selection are already worked out in the prior art. Direct labeling with fluorophores is also desirable, such as taught herein.

Conveniently, sequence selection is carried out using a hybridization procedure, preferably an in situ hybridization procedure, such as taught by Pinkel et al. (above cited).

Alternatively, hybridizations to membranes can be carried out where there are sample spots composed of DNA from a target chromosome, and other sample spots composed of DNA from the non-target chromosomes. Selection can proceed by carrying out hybridization to such a panel of samples, and identifying the probes which hybridize to the target, but not the non-target sample sites.

Based upon such examination and identification, the source clone colony for each so selected DNA sequence is identified and sampled. Such procedure is easily executed from procedure records which identify the source colony used for making each individual probe composition.

Cells of the sampled colonies containing the selected DNA sequences are fermented. Each colony sample can be separately cultured. Conditions of culturing can be as above described, if desired.

If more than one DNA sequence is identified and selected, it is preferred that each sequence be separately further processed as described herein. Those skilled in the art will readily appreciate that it is possible in some circumstances for two or more DNA sequences to be selected by practicing the foregoing procedural steps, although selection of only one is presently preferred.

The resulting cultured (fermented) colonies are then extracted using a procedure such as above indicated, thereby to isolate a usable quantity of each selected cloned DNA sequence. This cloned DNA sequence is complementary to a unique selected region of the one chromosome and incorporates at least one DNA repeated segment that is present in this region.

Typically and preferably, such a selected cloned DNA repeated segment containing sequence contains about 1,000 to about 12,000 bp, although the size can be larger or smaller as above indicated.

Typically, a product cloned DNA sequence contains at least about 18 mole percent of nucleotides which are deoxycytidine residues (based on total sequence nucleotide composition). In the case of the human genome, these DNA sequences typically have a higher A/T content than is observed in the average genomic sequences for man.

Such a product cloned DNA sequence so produced is unique, relative to all chromosomes of a multi-chromosomal genome, to one selected region of one chromosome thereof and has characteristics such as above indicated herein.

All methods of isolating chromosome specific, repeated DNA regional probes are ultimately bounded by the availability of divergent repeat sequences in the genome of interest. In order to isolate a sequence which can serve as a probe in a hybridization assay, a repeat sequence for the desired chromosome which is sufficiently different from similar repeats on any other chromosome to be discriminated by hybridization must exist. It is currently unknown whether such sequences exist on all human chromosomes. It is known that for some chromosomes, such as 13 and 21, a large number of the alphoid sequences are present on both chromosomes. Despite the isolation of a number of alphoid sequences present on chromosomes 13 and 21, there is no report in the literature of an alphoid DNA derived from either chromosome 13 or 21 which can be hybridized specifically only to the chromosome of origin in an in situ hybridization assay.

(D) Probe Production (1) General

Those skilled in the art will appreciate that many procedures are known to the prior art for associating a nucleotide sequence or sequences prepared as above described herein with a label or labels to make a probe.

Probes from such sequences preferably have labels that are capable of direct detection A direct label probe composition of excellent hybrid forming capacity and probe performance characteristics for regional chromosomal selective staining purposes in situ hybridization is provided when a probe composition is comprised of a mixture of DNA segments that are derived from a cloned DNA sequence of this invention. The segments are chemically bound to fluorophore groups through linking groups.

Thus, in a presently preferred and illustrative preparation procedure, the following steps are carried out:

(a) Fragmenting sequences comprising a selected regional chromosomal DNA into DNA fragments (or segments);

(b) Transaminating deoxycytidine nucleotides existing in the sequences (and consequently also in the derived segments) with a linking compound (as above described); and (c) Covalently bonding residual radicals of the so produced transaminated linking groups with a fluorescent compound (as above described).

This procedure and direct label probe compositions produced therefrom are described in the aforeidentified Bittner et al. parent U.S. patent application Ser. No. 585,876 and also is described in Bittner et al. U.S. patent application Ser. No. 762,912 filed on even date therewith and identified by the assignee's docket no. 30456. These applications and their teachings and disclosures are fully incorporated herein by reference.

(2) Fragmenting

The DNA segments used in probe compositions of this invention are derived from a starting cloned regional chromosomal DNA (prepared as above described herein) using a procedure taught in the aforecited Bittner et al. applications. The DNA segments preferably have an average size that is within a range of about 150 to about 600 bp with a presently more preferred average size being about 200 to about 400 bp, and a presently most preferred average segment size being about 300 bp.

(3) Transamination

In the transamination of polynucleotides, a minor percentage of the total deoxycytidine bases that are contained in the starting regional chromosomal DNA sequences and segments thereof become transaminated with an amino group of a difunctional linking compound (as above described) in the carbon 4 (C-4) atom position of the amino group of deoxycytosine nucleotides. The extent of such transamination is such that between about 1 and about 30 mole percent of all deoxycytidine nucleotides that are present in a starting mixture of DNA segments that is representative of a particular regional chromosomal DNA are thus substituted by such a linking group. Preferably about 2 to about 24 mole percent of all deoxycytidine nucleotides contained in such a mixture of starting DNA sequences or DNA fragments are thus transaminated. Thus, in general, about 0.2 to about 8 mole percent, and preferably about 0.2 to about 6 mole percent, of the total nucleotides present in the DNA fragments or sequences are transaminated. All such transaminations involve substantially only deoxycytidine nucleotides.

The most effective percentage of transamination in any given instance is typically influenced by the particular fluorescent label moiety to be used. Since the average number of base pairs present in a sequence is preferably at least about 150, as above indicated, each sequence is thus preferably substituted by at least one such linking group during the transamination procedure, as desired.

The transamination can be conveniently accomplished under aqueous liquid phase conditions in the presence of a bisulfite catalyst as a taught in the aforereferenced Bittner, et al. applications.

In the present transamination procedure, the bisulfite is conveniently introduced in the form of an alkali metal salt, with sodium and potassium being preferred alkali metals.

The present transamination reaction is carried out or continued until a desired extent of transamination of the starting DNA sequence or segment mixture is obtained. In general, the maximum extent of transamination is determined by the level of transamination which causes, or begins to cause, either an adverse effect upon the complementary character of the nucleotide sequences or segments involved, or an increase in the amount of non-specific association of the subsequently labeled probe with target DNA or other constituents of a target DNA, such as exist in a specimen, slide preparation or the like, during hybridization using a probe composition of this invention.

A mixture resulting from a transamination procedure that is in accord with the teachings of the present invention can be conventionally further processed. A present preference is to dialyze such a product mixture, against a dilute aqueous buffer, such as sodium borate, tris(hydroxymethyl)aminomethane (TRIS), or the like at a pH of about 8 using a conventional dialyzing membrane and ambient temperatures.

The resulting mixture of transaminated nucleotide sequences or segments is then conveniently precipitated from the so dialyzed mixture, and the sequence is then separated from the supernatant by filtration, centrifugation, or the like.

(4) Transamination with Chaotrope

This invention provides a preferred transamination procedure which is carried out in the presence of a chaotrope anion in the aqueous transamination medium. Such chaotrope anion maintains and/or prolongs nucleotide sequence denaturation during the transaminating. The chaotrope anions provided by the present invention enable one to maintain the DNA sequences undergoing aqueous bisulfite catalyzed transamination in a substantially single stranded or denatured state. Unless such a state exists, it is very difficult, if not impossible, to transaminate DNA uniformly and controllably, and to regulate the number of sites in DNA sequences or segments where the linking group will be substituted on the deoxycytidine nucleotides.

While the present method of accomplishing transamination with the herein provided chaotropes is illustrated by reference to the production of the present inventive probe compositions, it will be appreciated that this method has general suitability for transamination of deoxycytidine nuclei in polynucleotide DNA containing at least one deoxycytidine nucleotide per molecule under aqueous liquid phase bisulfite anion catalyzed conditions with an amine radical containing compound as such as a linking compound as hereinabove defined which contains at least one functional (i.e., reactive) radical with one of such radicals being an amino group.

Thus, the chaotrope transamination technique provided by this invention utilizes a starting DNA nucleotide sequence that contains at least one deoxycytidine nucleotide per nucleotide sequence molecule. The technique is carried out in an aqueous medium by contacting the sequence with dissolved bisulfite, dissolved trihaloacetate anionic chaotrope, and dissolved functional amino-group containing compound. By regulating the contacting conditions, and the quantity of chaotrope anions present, the degree of sequence transamination can be controlled so that a statistically desired percentage of the total deoxycytidine nucleotide moieties present in each sequence are transaminated. Preferably a polynucleotide that is to be transaminated in the presence of the anionic chaotrope is preliminarily subjected to a thermal denaturation procedure. For example, starting polynucleotide is boiled in water for a time of about 1 to about 12 minutes followed by chilling to a temperature that is preferably below about 4° C. The chaotrope anion then maintains the polynucleotide in a denatured condition during the subsequent transamination reaction.

Although DNA may heretofore have been transaminated with aqueous bisulfite and amine, so far as now known, a transamination of DNA with such chaotrope anion has never previously been carried out.

In the present context, a chaotrope is an ion that has a relatively large radius, a negative charge, and a low charge density which effectively alters the configuration of a nucleic acid. In a transamination using aqueous bisulfite solution, the chaotrope functions to promote, maintain, and/or prolong a DNA sequence in at least a partially single-stranded (i.e., denatured) form.

In transaminating a mixture of DNA sequences or segments with aqueous bisulfite solution, a chaotropic salt denaturant or an organic solvent denaturant might be desirable in general theory, but, in practice, such a denaturant is difficult to find or to use either because it induces crystallization of one or more the components present in the transaminating aqueous medium and thus undesirably reduces their effective concentration, or because it is reactive with one or more of the components present. Surprisingly, the chaotrope anions of the present invention do not exhibit such disadvantages.

In a DNA transamination with aqueous bisulfite, only trihaloacetates have surprisingly now been found to have a suitable balance of properties for use as DNA denaturing chaotrope anions. While a trifluoroacetate anion is useful as a chaotrope over a wide concentration range, a trichloroacetate anion is useful only at concentrations below about 1M because of a tendency for this anion to cause crystallization of one or more of the components present in the aqueous transamination medium at higher concentrations. However, the trichloroacetate anion can be used in admixture with the trifluoroacetate anion. No other suitable such DNA transaminating denaturing chaotropes are known.

The trihaloacetate anions employed in the present transamination procedure as chaotropes are conveniently introduced into the aqueous transamination medium as alkali metal salts, with sodium and potassium cations being preferred alkali metals. The trihaloacetate anions are selected from the group consisting of trichloroacetate, trifluoroacetate, and mixtures thereof. Trifluoroacetate anions are preferred for reasons of solubility characteristics and relatively small anion size.

After transamination between the DNA and the linking compound, one functional group of the linking compound remains free to undergo further reaction with a label group containing compound which itself contains a reactive group that is reactable with such remaining functional group.

With the added presence of the trihaloacetate chaotrope anion with the bisulfite, transamination reaction variables can be varied within ranges such as are illustratively shown in Table II below. Thus, one can achieve a desired degree of transamination with a given linking compound reactant at any desired level ranging from complete (100%) to partial (for example, about 0.5 mole percent or less) transamination of deoxycytidine nucleotide residues present in a nucleotide sequence. However, for present intermediate transaminated sequences which are intended for probe production purposes, the maximum level of transamination is usually not more than about 30 mole percent of such residue.

TABLE II

Variables in DNA Transamination with Amine, Bisulfite and Trihaloacetate

| ID No. | Variable | Range Broad | Preferred |
| --- | --- | --- | --- |
| 1. | DNA concentration | 25–1000 µg/ml | 100–400 µg/ml |
| 2. | Temperature | 20–60° C. | 25–45° C. |
| 3. | pH | 4.5–7.5 | 7.0–7.2 |
| 4. | Reaction time | 1–72 hours | 1–16 hours |
| 5. | Total trihaloacetate conc. | 1M–4M | 4M |
| 6. | Total linking compound concentration | 1M–3M | 3M |
| 7. | Bisulfite anion concentration | 0.4–1.4M | — |

While the present transamination reaction with the chaotrope can be carried out over a relatively wide pH range of about 4.5 to about 7.5, the use of a pH in the range of about 4.5 to about 6.0 has been found to induce a competing side reaction that results in converting some deoxycytidine residues to deoxyuridine residues. Such a conversion is generally undesirable since it tends to result in a product DNA sequence that is no longer completely complementary to the same target DNA sequence. Therefore, in the practice of probe making, it is preferred to use during a preferred transamination that is in accord with the teachings of this invention pH values in the range of about 6.5 to about 7.5, and more preferably a pH about 7±0.2.

The present transamination reaction with chaotrope is carried out or continued until a desired extent of transamination of the starting sequence or segment mixture is obtained. In general, the maximum extent of transamination achieved is determined by the level of transamination which causes, or begins to cause, an adverse effect upon the complementary character of the nucleotide sequence(s) involved. Typically and illustratively, the time period is generally in the range shown in above Table II.

A mixture resulting from a transamination that is in accord with the present invention can be conventionally further processed, as above indicated. A present preference is to dialyze such a product mixture against an alkali metal lower monoalkanoate to separate therefrom substantially all nonalkanoate salt anions present. Preferred alkali metals again are sodium and potassium, and preferred lower monoalkanoates contain less than five carbon atoms each.

The resulting transaminated nucleotide sequence is then conveniently precipitated from the so dialyzed mixture, and the sequence is then separated from the supernatant by filtration, centrifugation, or the like.

In general, a transamination that is carried out in accord with this invention for purposes of making a probe composition of this invention is continued until the weight percentage of the aminated nucleotides present is within the above indicated ranges.

Bisulfite catalyzed transamination of polynucleotide (i.e., DNA sequences and/or DNA segments) with chaotrope anions as taught herein has been found to make possible the production of a new and heretofore unavailable class of transaminated polynucleotides. This class comprises:

(a) an aqueous solution containing at least about 20 µg/ml of polynucleotide dissolved therein, (b) said polynucleotides being characterized by containing not less than about $1 \times 10^{10}$ complementary sequential DNA copies per µg of said polynucleotides (dry weight basis), and (c) said polynucleotides being substituted on about 12 to about 30 mole % of the deoxycytidine nucleotides thereof with a linking group.

In this class, a higher percentage of transamination of concentrated segmented DNA in aqueous solution has been achieved for polynucleotides having the relatively low complexity indicated by the stated number of complementary sequential copies per microgram (µg) of polynucleotide than is achievable by prior art teachings. Thus, use of thermal denaturation as hereinabove described is useful for accomplishing denaturations, but such denatured polynucleotides tend to reanneal and reform into the starting or initial double stranded condition rather rapidly during the subsequent transamination. Hence, the maximum level of transamination with linking compound on deoxycytidine nucleotides achievable with thermal denaturation (without the present chaotropes) and bisulfite catalysis is believed to be only from about 7 to not more than about 12 mole percent (based on total deoxycytidine nucleotides present in the polynucleotides being so transaminated).

The presence of added chaotrope to the transamination medium after initial thermal denaturation serves to keep the polynucleotides in a single stranded state during the transamination reaction, thereby permitting not only the controlling of the transamination, but also the achievement of the higher desired levels of transamination with linking compound on deoxycytidine nucleotides than was heretofore possible.

Since high concentrations of transaminated polynucleotides are desired to permit the making of product aqueous probe compositions containing high probe concentrations, and since the cloned DNA sequences that are produced by the teachings of the present invention commonly have (before or after fragmentation) about $30 \times 10^{10}$ to about $40 \times 10^{10}$ complementary sequential DNA copies per µg of such sequences (dry weight basis) this chaotropic amination procedure and resulting new intermediate transaminated product (as above described) are important aspects of this invention.

Thus, in a presently preferred bisulfite catalyzed transamination with chaotrope, the polynucleotide being transaminated in the aqueous reaction medium is in the form of DNA segments having average sizes in the range of about 150 to about 600 bp. The concentration of such segments is at least about 20 µg/ml, and such segments contain not less than about $1 \times 10^{10}$ complementary sequential copies per µg of said segments (dry weight basis). Preferably such segments are produced by fragmenting a cloned DNA sequence produced by the practice of this invention that is complementary to one region of one chromosome.

(5) Fluorescent Compound Bonding

A resulting transaminated amine substituted nucleotide derivative prepared as above described is available for covalently bonding with a reactive fluorophore radical-containing fluorescent compound, such as above described, with such fluorescent compound reacting with a terminal functional amino or carboxyl radical associated with the residue of the linking compound (i.e., the linking group) that has now been transaminated into a deoxycytidine moiety as above described. The covalent bonding procedure described in the aforereferenced Bittner et al. applications is suitable and is presently preferred.

In the reaction, covalent bonding is believed to occur between a reactive group present in a starting fluorescent compound and the terminal reactive group of a transaminated linking group (derived from a linking compound) that is associated with a DNA sequence. At least one terminal group of one linking group per molecule is reacted with the fluorescent compound employed. Typically, about 20 to about 100 mole percent of the terminal sites of the transaminated linking groups are reacted and thus fluorescently labeled. Preferably, for efficiency reasons, at least about 80 weight percent thereof are so labeled, and most preferably about 90 weight percent thereof are so labeled.

Residual labeling compound not covalently attached to the probes at the end of the reaction time can be removed by a variety of methods, such as taught in the above referenced Bittner et al applications.

The resulting reaction product of the transaminated DNA sequences and the selected fluorescent compound comprises a probe composition.

(E) Utilization

DNA sequence was produced by the cloning procedure provided by the present invention as specifically described in Example 12 below. The fragmented segments (averaging 300 bp. each) were then transaminated with ethylene diamine as described herein and as illustrated in Example 16 below. Thereafter, the transaminated DNA segment mixture was labeled with biotin as described in Example 17 below. The hybridization procedure was carried out as described in Example 17 below, and the subsequent detection was accomplished by post-hybridization incubation with fluorescein conjugated to streptavidin using the procedure described in Example 4 below. The photograph was taken with a filter specific for fluorescein fluorescence (identified as filter 4 in Table V of Bittner et al. copending application) and no staining (i.e., light emission from fluorophores emitting at a different light frequency), such as from a fluorescent counterstain or the like, is visible.

Thus, this starting sequence is suitable for use as a probe even when indirect labeled.

The metaphase chromosomes are dispersed. Here, these chromosomes and nuclei are shown after in situ hybridization under hybridizing conditions with a probe composition of this invention which is specifically hybridizable with the centromere region of human chromosomes #8. The hybridization procedure described in Example 17 below was followed. This probe composition employs the same DNA segment mixture that was employed in the indirect labeled probe composition. This segment mixture was identically transaminated, but then was labeled with the fluorophore CTMR using the inventive procedure described in Example 17 below. No further processing to produce fluorophore development was carried out as is necessary with indirect label probes. This photograph was taken with a filter specific for the CTMR fluorophore. (Filter #7 of Table V of the cited copending Bittner et al. application).

DAPI was used to treat this specimen as described in Example 17 below. The filter employed by this photograph was no. 1 in Table V of the copending Bittner et al. application. This DAPI counterstain clearly shows the location of both the metaphase and the interphase nuclei. It can further be seen that the staining is localized at the centromeres of the chromosomes.

Embodiments

The present invention is further illustrated by reference to this following examples.

Example 1. Template for Enzymatic Amplification DNA Derived from a Chromosome Library A plasmid library for human Chromosome 8 was obtained from Lawrence Livermore National Laboratories (LLNL). It was a derivative of the bacteriophage lambda library deposited with the ATCC as #57702. Cloning of this chromosome specific library into bacteriophage vectors is detailed in; M. A. Van Dilla et al. in *Bio/Technology* 4:537–552 (1986). The bacteriophage libraries for the various human chromosomes are available from the American Type Culture Collection. The resulting libraries were then amplified by growth on an *E. coli* host strain. The amplified phage was purified, and their DNA was extracted. This DNA was digested with the restriction enzyme Hind III. Insert DNA was purified away from the lambda vector DNA and cloned into the Hind III site of the plasmid vector pBS (Stratagene, La Jolla, Calif.). This is a high copy number, ampicillin resistant plasmid derivative of pBR 322. The resulting plasmids were transformed into an *E. coli* strain, DH5α (Bethesda Research Libraries, Gaithersburg, Md.). The derived plasmid library was stored as 1 ml aliquots of frozen cells. These vials were used as the primary source for the production of seed stocks for fermentation.

An expansion by fermentation of the original library obtained from LLNL was made to provide working stocks for both fermentation and library screening. The preparation of expanded seed stocks from the original library provided by LLNL is accomplished as described in Example 1 of Bittner et al. parent U.S. Ser. No. 585,876 and in Example 1 aforereferenced Bittner et al. U.S. Ser. No. 762,912 filed on even date herewith. The production of large quantities of DNA from this library, by fermentation and extraction is accomplished as described in Example 1 of such U.S. Ser. No. 585,876 and in Example 1 of such aforereferenced copending Bittner et al. U.S. Ser. No. 762,912.

Example 2. Synthesis of Oligonucleotide Primers

A degenerate mixture of synthetic oligonucleotides was prepared. The extent of degeneracy is sufficient to allow the oligonucleotides to function as primers on most known alphoid DNA sequences and they were therefore expected to prime the alpha satellite region of the centromere of Chromosome 8.

This oligonucleotide mixture was comprised of two oligonucleotides which are each identified as follows:

Primer 1: GAA GCT TA (A/T) (G/C)T(C/A) ACA GAG TT(G/T)AA
Primer 2: GCT GCA GAT C(A/C)C (A/C)AA G(A/C/T)A GTT TCT Example 3. Enzymatically Amplifying Using Single Chromosome Template Using the Chromosome 8 library prepared as described in Example 1 (above) as the template, and the oligonucleotide mixture prepared as described in Example 2 (above) as the primer composition, enzymatic amplification was carried out as follows:

Alpha satellite DNA regions of the DNA extracted from the pBS8 library were enzymatically amplified and biotinylated by a so-called polymerase chain reaction (PCR) as described in Mullis, K. B., et al. in, *Methods in Enzymology* 155:355–350 (1987). The polymerase, nucleotides and salts used were from the Perkin Elmer-Cetus GeneAmp kit, and are used at the concentrations recommended by the manufacturer. The primers (see Example 2) were composed of 7 nucleotides at the 5' end which specify a restriction enzyme recognition site and 17, 3' nucleotides based on the alphoid sequence mixtures which flank the 170 base pair alpha satellite repeat region of the centromere. Primers were present in the reaction mix (100 μl) at a concentration of 1 μM). The primers were compounded with 2.5 units of $T_{aq}$ polymerase in a buffer containing 20 mM Tris-HCl pH 8.3, 50 mM KCl, 1.5 mM Mg $Cl_2$ and 0.01% gelatin.

Two different sized templates from the pBS8 library were prepared; one consisted of sonicated double-stranded DNA (approximately 300–500 base pairs in size) and the other was a Hind III restriction digest. Restriction digested template DNA was prepared by incubating 5 µg of pBS8 library DNA in a 50 µl solution containing 20 mM Tris-HCl (pH 7.4), 10 mM MgCl$_2$, 50 mM CaCl, and 20 units of restriction enzyme Hind III (New England Biolabs, Beverly, Mass.) for 1 hour at 37° C. The digested DNA was extracted 25 µl of phenol, then 25 µl of chloroform was added and the solution reextracted. The aqueous phase was recovered after centrifugation for 1 minute at 10,000 xg, and DNA was precipitated from this solution by the addition of 5 µl of 3M sodium acetate and 150 µl of ethanol. Precipitate was recovered by centrifugation for 5 minutes at 10,000 xg and vacuum dried. The resulting DNA digest was resuspended in 50 µl of water. Mechanically sheared DNA template was prepared by sonication. A Branson Sonifier 450 (Danbury, Conn.) is employed for this step. Four milligrams of the purified plasmid DNA prepared in Example I above is resuspended in two mls of water in a 12×75 mm polypropylene tube. The tube is immersed in a dry ice/ethanol bath to prevent boiling during sonication. The micro tip of the sonication device is immersed in this solution until the tip is 2–5 mm from the bottom of the tube. Sonication is carried out discontinuously with an 80% duty cycle (on 80% of time, off 20% of time) for a period of 5 minutes. Following sonication, the solution of DNA is transferred to a 16×100 mm screw cap polypropylene tube. The DNA fragments are precipitated by addition of 0.2 ml of 3M sodium acetate (pH 5.5) and 4 ml of ethanol. The precipitate is recovered by centrifugation for 5 minutes at 8,000 x g. The supernatant is removed and the pellet is vacuum dried. The sonicated DNA is resuspended in water at a concentration of 3 mg/ml.

Reaction mixtures consisted of 100 µl volume using 0.75 µg of either template DNA, 200 µM each of dCTP, dGTP, dATP, 100 µM dTTP, 100 µM biotin-11-dUTP, 1 µM each of the two synthetic oligonucleotide primer mixtures. The reaction mix was overlaid with 100 µl of sterile mineral oil and the amplification was performed automatically using the Perkin Elmer Cetus (PEC) DNA Thermal Cycler. Twenty five cycles of amplification were used. Each of the first twenty four cycles were one minute denaturation at 92° C., 2 minute template priming at 37° C., and 3 minute polymerization at 72° C. The final cycle was a 7 minute polymerization period at 72° C. followed by cooling to 4° C. The PCR products were extracted with phenol-chloroform, precipitated with ethanol and resuspended in 100 µl of sterile water.

Example 4. Evaluation

Each of the PCR products was tested by in situ hybridization. The target DNA was from normal white blood cells that were arrested in metaphase and fixed on microscope slides. Each slide was placed in a denaturing solution containing 70% formamide/0.3M NaCl/30 mM sodium citrate pH 7 at 70° C. for 5 minutes. The slides were then dehydrated by passing through 70%, 85% and 100% ethanol baths (2 minutes each) and air dried.

Each 10 µl hybridization mix contained 1 µl of PCR amplified product in 55% formamide/10% dextran sulfate/0.15M NaCl/15 mM sodium citrate/1 µg sonicated salmon sperm DNA (used as a carrier). The hybridization mix was denatured at 70° C. for 5 minutes and placed on ice. The slide was prewarmed to 37° C. and the hybrid mix was applied directly onto the slide, covered with a glass coverslip, sealed, and incubated overnight at 37° C. in a humid chamber. The unreacted amplified DNA was removed by three 15 minute washes in a solution of 50% formamide/0.3M NaCl/30 mM sodium citrate pH 7, followed by a single 15 minute wash in 0.3M NaCl/30 mM sodium citrate and then a 15 minute wash in 0.1M sodium phosphate/0.1% NP40 detergent (Octylphenoxypolyethoxyethanol, which is a nonionic surfactant sold by Calbiochem, La Jolla, Calif.), all at 45° C. The slide was incubated in a solution of fluorescein labeled streptavidin (5 µg/ml) in 0.1M sodium phosphate buffer containing 5% (v/w) Carnation Instant Milk for 20 minutes at room temperature. The slide was washed three times in 0.1M sodium phosphate buffer at room temperature, 2 minutes per wash. 7.5 µl of a counterstain consisting of 0.2 µg/ml propidium iodide in an antifade solution was applied, allowing visualization of the nuclei and chromosome spreads. A coverslip was placed over the counterstained area and the slide was viewed with a fluorescence microscope.

The antifade solution is prepared as described in J. Immuno. Methods, 43, 349 (1981). 100 milligrams of p-phenylenediamine dihydrochloride (Sigma P 1519) is dissolved in 10 milliliters of phosphate buffered saline solution. The pH of this solution is adjusted to pH 8 with a bicarbonate buffer solution prepared by adding 0.42 g NaHCO$_3$ to 10 milliliters of water then adjusting the pH to 9.0 by the addition of 50% (w/v) NaOH. The pH adjusted solution of p-phenylenediamine dihydrochloride is added to 90 milliliters of glycerol and the resulting solution is filtered through a 0.22µ filtration device. This solution is stored in the dark at −20° C.

The results of the hybridization showed approximately eight discrete signals of varying intensity within the nuclei as well as in the metaphase chromosome spreads. The nonspecific hybridization of the PCR products to chromosomes other than human Chromosome 8 could arise from two very different causes. The nonspecificity could be a true function of the sequences being produced. This would be expected if the sequences being amplified were in fact present on chromosomes other than Chromosome 8, but were less abundant on the other chromosomes. The other means of producing nonspecific hybridization could be production of PCR products which were the result of incomplete synthesis of the template. Such short products would not contain sufficient DNA to insure that they bound faithfully to the desired target. To differentiate between these possibilities, it was decided to remove small (<170 bp) DNAs from the reaction products, and test the remaining larger DNA products for specificity. To remove short products from the probe mixes, the PCR products were purified on a column which fractionates DNA on the basis of its size. Each of the polymerase chain reaction DNA products were individually purified on a Mono Q column (an anion exchange column manufactured by Pharmacia) using the Fast Performance Liquid Chromatography (FPLC) automated system. A 40 µl sample was analyzed using a 0.075%/min. gradient beginning with 60% 0.4M NaCl/20 mM Tris pH 8.3 to 75% 1.4M NaCl/20 mM Tris pH 8.3. The flow rate was 0.25 ml/min., one milliliter fractions were collected, and monitored for absorbance at 260 nm. Three populations of larger than monomer sized DNA were isolated from the PCR product using sonicated DNA as a template (171 bp, 513 bp and 1026 pb). The PCR products derived from the Hind III digested DNA were of only two sizes (513 bp and 1026 bp). Each population of PCR product was ethanol precipitated and resuspended in 25 µl of sterile water. Each of the isolated DNA populations were tested for chromosome 8 specificity using in situ hybridization.

A 2.5 µl sample of the fractionated PCR product was used as a probe in an in situ hybridization assay as described above in this Example.

All populations of amplified DNA isolated from the PCR reaction using sonicated DNA as template demonstrated a specific signal for the centromere of chromosome 8 in both the nuclei and chromosome metaphase spreads with varying intensities of signal. Only the 1026 bp component generated from the polymerase chain reaction using the Hind III digested DNA template produced a specific signal for chromosome 8. It was thus clearly possible to generate a mixture of repeat DNA sequences specific for chromosome 8 via this method. Next, we proceeded to capture individual DNA sequences.

Example 5. Cloning of Centromere of Chromosome 8 Using Enzymatically Amplified Products DNA sequences specific for the centromere of human Chromosome 8 were generated using an enzymatic amplification procedure with the sonicated pBS8 library prepared as described in Example 3 (above) as a template. The reaction volume was 100 µl of 20 mM Tris-HCl pH 8.3, 50 mM KCl, 1.5 mM $MgCl_2$ containing 0.75 µg of sonicated pBS8 double stranded DNA, 200 µM each of dCTP, dGTP, dATP, and dTTP, 1 µm of each of the synthetic oligomers primers of Example 2 (above) which hybridize to the alpha satellite region of the centromere and 2.5 Units of Taq polymerase. The reaction mix was overlaid with 100 µl of sterile mineral oil and the amplification was carried out automatically using the Perking Elmer Cetus (PEC) DNA Thermal Cycler. Twenty five cycles of amplification were used. Each of the first twenty four cycles were one minute denaturation at 92° C., 2 minute template priming at 37° C., 3 minute polymerization at 72° C. The final cycle was a 7 minute polymerization period at 72° C. followed by cooling to 4° C. The amplified material was phenol chloroform extracted, ethanol precipitated and resuspended in 100 µl of sterile water. A 5 µl aliquot was analyzed on a 1% agarose gel containing 0.04M Tris-Acetate, 1 mM EDTA and 1 µg/ml ethidium bromide at 150 V for 1 hour. Three different sized DNA products were identified; 180 bp, 369 bp and 738 bp DNA.

A 40 µl aliquot of the amplified DNA product was purified and fractionated on a Mono Q column (anion column manufactured by Pharmacia) using the Fast Performance Liquid Chromatography (FPLC) automated system as described in Example 4 (above). Three populations were again separated from the polymerase chain reaction mixture. The third population containing the largest quantity of material was ethanol precipitated and resuspended in 20 µl of sterile water.

A 10 µl aliquot of the third population was digested using 10 Units each of PstI and Hind III in 50 mM Tris-HCl pH 8.0, 10 mM $MgCl_2$, 50 mM NaCl at 37° C. for one hour. The material was phenol-chloroform extracted, ethanol precipitated and resuspended in 10 µl of sterile water. 10 µl of PstI and Hind III restriction digested M13mp18 vector was also prepared in the same manner.

The resulting purified, restricted products of the enzymatically amplified reaction were cloned into the restricted M13mp18 vector by methods described in Sambrook, et al. in "Molecular Cloning: A Laboratory Manual", pp. 4.2–4.33. Cold Spring Harbor, N.Y., 1989. The cloned DNA was introduced into host JM101 E. coli bacteria by electroporation using a Gene Pulser (Bio-Rad. Richmond, Calif.) apparatus, according to the manufacturer's recommendations. Specifically:

The restriction digested PCR product was then ligated with the digested M13mp18 vector. 50 µl ligation reactions contained 0.5 µg of restriction enzyme-digested M13mp18 vector in 50 mM Tris-HCl pH 7.6, 10 mM $MgCl_2$, 1 mM ATP, 1 mM DTT, 5% (w/v) polyethylene glycol-8000, 2 units T4 ligase with either 0.5 µl, 1 µl, or 2 µl of digested PCR product. The reaction was incubated at 37° C. for two hours. The ligation product was phenol-chloroform extracted, ethanol precipitated, dried and resuspended in 15 µl of sterile water.

E. coli JM101 cells were prepared for electroporation. A colony from a streak plate of JM101 was grown in 100 ml of TYE broth which contained 10 g/l Tryptone, 5 g/l Yeast Extract, 5 g/l NaCl 3 g/l KCl overnight in an aerated 37° C. water bath. 500 ml of TYE broth was inoculated with 5 ml of the overnight JM101 culture. The cells were grown aerated at 37° C. until the absorbance at 600 nm was 0.5 to 1.0 OD. The cells were placed on ice for 30 minutes. The culture was centrifuged for 15 minutes at 4000 xg to pellet the cells. The cell pellet was then resuspended in 500 ml of 1 mM HEPES (N-2-Hydroxyethylpiperazine-N'-2-ethane-sulfonic manufactured by Gibco Laboratories) pH 7 and centrifuged again. The cells were resuspended in 20 ml of 1 mM HEPES/10% glycerol and centrifuged again. The cells were then resuspended in 1 mM HEPES/10% glycerol at a concentration of approximately $3 \times 10^{10}$ cells/ml. The cells were aliquoted, frozen in liquid nitrogen and stored at 80° C. until needed for the electro-transformation.

An electro-transformation was performed for each of the ligations noted above with a Gene Pulser apparatus (Bio-Rad, Richmond, Calif.) according to the manufacturer's recommendation. The prepared cell suspension was thawed at room temperature and then kept on ice until needed. 40 µl of the cell suspension and 1 µl of a particular ligation were mixed and placed on ice for one minute. The mixture of cells and ligated DNA was added to a cold 0.2 cm electroporation cuvette. The Gene Pulser (Bio-Rad, Richmond, Calif.) apparatus was set at 25 uF and 2.5 kV. The Pulse Controller was set at 200 Ohms. The sample was pulsed once at the noted settings. Immediately after the electroporation, 0.5 ml of media containing 2% Bacto tryptone, 0.5% Bacto yeast extract, 10 mM NaCl, 2.5 mM KCl, 10 mM $MgCl_2$, 10 mM $MgSO_4$, 20 mM glucose was added to the cuvette. The cell suspension was removed from the cuvette and incubated at 37° C. until plated.

The resulting transformed cells were cultured on layers of E. coli bacteria spread over the surface of a nutrient agar plate by methods described in Sambrook, J., et al "Molecular Cloning: A Laboratory Manual", pp. 4.2–4.33.

250 µl of the electroporated cells were placed in 3 ml of media containing 7 g/l Bacto-Agar, 8 g/l Tryptone, 5 g/l yeast extract, 5 g/l NaCl, 200 µg of X-gal (5-bromo-4-chloro- 3-indoly-B-D-galactoside (Bethesda Research Laboratories, Gaithersburg, Md.) and several drops of an overnight JM101 culture. The entire mixture was overlaid on a 1.5% Bacto-Agar plate containing 16 g/l Tryptone, 10 g/l yeast extract and 5 g/l M NaCl (YT agar plate). The mixture was allowed to solidify at room temperature and then incubated at 37° C. overnight.

Plaque forming colonies of cells demonstrate a successful ligation of the enzymatically and fixed product into the vector. Colony producing plaques were picked from each of the plates at random and placed in 2 ml of 2 YT media (16 g/l Tryptone, 10 g/l yeast extract, 5 g/l NaCl). Two drops of an overnight JM101 culture was added to the media and the culture allowed to incubate overnight aerated at 37° C. Results are as shown in Table III below.

TABLE III

Relationship Between Insert and Plaque Number

| Amount of Amplified Insert | Number of Plaque Forming Colonies |
| --- | --- |
| 0.5 µl | 17 |
| 1.0 µl | 54 |
| 2.0 µl | 23 |

Example 6. Sample Plagues

As the vector is a phage, the terminology for the colony of descendants of the original transformation is a plaque. The results are formally the same as for a plasmid. Thus, there are copies of episomal genetic elements bearing the same fragment of cloned DNA.

The recombinant DNA insert-containing bacteriophage plaques resulting from the procedure applied in Example 5 (above) were sampled by inserting a sterile toothpick into the plaque, and then transferring phage and infected cells from the plaque into a tube containing two milliliters of sterile 2 YT media.

Example 7. Separately Culture and Extract Sampled Vector DNA

The sampled host cells obtained in Example 6 were allowed to incubate overnight with agitation at 37° C. The cultures were centrifuged in the Eppendorf Microfuge for 10 minutes. One milliliter of supernatant was stored at 4° C. as a phage stock. 250 µl of buffer containing 2.5M NaCl, 10% polyethylene glycol 6000, 0.015M NaEDTA pH 8.0, 40 µg of heat inactivated RNase was added to the second milliliter of supernatant and incubated at 4° C. for 2 hours. The samples were centrifuged for 10 minutes in the Eppendorf microfuge and the supernatant was discarded. The pellet for each sample was resuspended in 50 µl of Phage Coat Digestion buffer containing 0.2% Sarkosyl, 10 mM Tris pH 8.0, 1 mM NaEDTA, 10 µg of Proteinase K and incubated for 1 hour at 55°–65° C. Each sample was phenol-chloroform extracted, ethanol precipitated, dried and resuspended in 10 µl of sterile water.

Example 8. Label Each Vector DNA Forming a Probe Class

Each such fermented and extracted vector DNA material produced as described in Example 7 was labeled by subjecting 2.5 µl of each isolated DNA to enzymatic amplification and biotinylation as described in Example 3 above. Probe compositions for fifteen individual colonies were prepared.

5 µl of each composition was analyzed on a 1% agarose gel containing 0.04M Tris-Acetate 1 mM EDTA and 1 µg/ml of ethidium bromide. A 123 bp DNA ladder (manufactured by Bethesda Research Labs, Gaithersburg, Md.) was used as a standard for size determination. Results obtained are shown in Table IV below:

TABLE IV

Relationship to Sequence Size to Clone Number

| Size Range (base pairs) | Number of Clones |
| --- | --- |
| 300–500 | 4 |
| 550–750 | 2 |
| 900–1200 | 4 |
| 1800–3000 | 5 |

Example 9. Hybridize Each Probe with Samples of Genome as Target

Each of the probe compositions of Example 7 was hybridized to a target sample of the human genome. One µl of each of the probe compositions was evaluated in an in situ hybridization as described in Example 4 (above).

The product hybridized probe samples of Example 1 were examined and clones which produced probes giving signals specific to a particular chromosome pair were noted. The in situ hybridization revealed that 13 of 15 clones were chromosome 8 specific.

Results are presented in the following Table V.

TABLE V

In Situ Hybridication Results Using Biotin Incorporated PCR Product from Individual M13 Clones as Probe

| Clone | Insert Size | Number of Signals | Nuclear Background |
| --- | --- | --- | --- |
| 1-1 | 1100 | 6 strong signals | low |
| 1-2 | 369 | 4 strong signals | moderate |
| 1-3 | 550 | 2 signals | high |
| 1-4 | 2200 | 2 din signals | very high |
| 1-5 | 269 | 2 dim signals | very high |
| 2-1 | 3000 | 2 signals | high |
| 2-2 | 550 | 2 signals | high |
| 2-3 | 738 | 0 | low |
| 2-4 | 984 | 0 | low |
| 2-5 | 1800 | 2 signals | moderate |
| 3-1 | 980 | 2 signals | low |
| 3-2 | 369 | 2 strong | moderate |
| 3-3 | 984 | 2 strong signals | high |
| 3-4 | 3200 | 4 signals | low |
| 3-5 | 369 | 2 signals | high |

From the information shown in the foregoing Table V, three clones were chosen which gave good signal intensity and specificity. These clones contained a 550, 1100, and 3000 base pair insert, respectively, It was concluded that enzymatically amplified sequences that are cloned as herein above described can at least in most cases be used as templates to generate DNA sequences which can be labeled and used as centromere-specific probes for particular chromosome.

Two of these M13 clones, 1-1 and 2-2 were tested for their ability to serve as probes when transaminated and biotinylated by the chemical methods herein provided (see examples below).

Example 10. Isolating Repeated DNA Sequence, Sampling, Fermenting and Extracting Once colonies which give signals primarily for a single pair of chromosomes are known (which is simply done by recordkeeping) one proceeds to culture an additional quantity of the vector. This was done as follows:

Cultures of the M13 clones 1-1 and 2-2 were prepared as follows. *E. coli* JM101 was cultured overnight at 37° C. in YT Broth. The JM101 culture was diluted 1/100 in 3 ml of 2 YT Broth and allowed to grow for 3 hours. $10^7$ phage were added to 0.5 ml of this culture and allowed to grow for 3 hours and then transferred to 500 ml of 2 YT Broth in a 2.4 liter Fernbach flask. This culture was allowed to grow overnight at 37° C. with constant agitation. At this point, the bacterial cells contain significant amounts of the circular double-stranded (replicative form) of the bacteriophage DNA. This form of the DNA can be recovered by the same procedure as is used for the recovery of plasmid DNA.

DNA was extracted from all of the cultured cell masses using the following protocol. Cells were recovered from the growth medium by centrifugation in 500 ml polypropylene centrifuge bottles. The bottles were capped and centrifuged at 7,000 g for 10 min in a refrigerated centrifuge. The wet cakes were recovered after discarding the supernatant. Cell paste was resuspended in 40 ml of 50 mM glucose (filter sterilized, 10 mM NaEDTA (pH 7.5–8.0), and 25 mM Tris-HCl (pH 8.0). The resuspended cells were lysed in 80 ml of 0.2M NaOH and 1% (w/v) SDS. The cell lysate was treated with 60 ml of a solution containing 55.5 ml of glacial acetic acid and 147.5 grams of potassium acetate per 500 milliliters. These solutions were mixed thoroughly, resulting in the production of a flocculent precipitate. The supernatant was removed from the flocculent precipitate and this supernatant was centrifuged for 15 minutes at 7000 x g to remove residual precipitate.

Nucleic acid was precipitated from the supernatant with 180 ml of ethanol followed by centrifugation for 10 minutes at 7000 x g. The nucleic acid pellets were resuspended in a total of 10 milliliters of a solution containing 50 mM Tris-HCl (pH 8.0), 100 mM sodium acetate. The nucleic acid was then extracted with 5 ml of neutralized phenol and 5 ml of chloroform and reprecipitated with 20 ml of ethanol. The thoroughly drained nucleic acid pellet was resuspended in 5.36 ml of water. The solution was transferred to a 15 ml polypropylene tube and 0.64 ml of 5M NaCl and 2.0 ml of 50% (w/v) PEG (M.W. 6000–8000) were added and mixed thoroughly. The solution was incubated on ice water for one hour and centrifuged for 10 minutes at 10,000 rpm. The pellet was resuspended in 5 ml of a solution containing 50 mM Tris-HCl (pH 8.0), 100 mM sodium acetate. To this solution was added 10 microliters of 10 milligram/milliliter pancreatic Ribonuclease A solution (heat treated to inactivate DNase). Enzymatic degradation of RNA was allowed to proceed for 30 minutes at room temperature. A 10 microliter portion of 20 milligram/milliliter Proteinase K solution was then added and incubated at 55° C. for three hours. The DNA solution was then extracted with 2.5 ml of neutralized phenol and 2.5 ml of chloroform and reprecipitated with 10 ml of ethanol. Precipitated DNA was collected by centrifugation for 15 minutes at 4500 x g. The resulting pellet was vacuum dried and then resuspended in 0.5 ml of water. DNA concentration was determined by fluorometry.

The DNA resulting from the fermentation of M13mp18 clones 1-1 and 2-2 consisted of approximately 7400 base pairs of M13mp18 vector DNA and approximately 1100 base pairs of insert in clone 1-1 and approximately 550 base pairs of insert in clone 2.

Example 11. Labeling Amplified DNA Sequences Forming Probe Composition

The enzymatically amplified products as produced in Example 3 were labeled to produce a prose composition by the following procedure:

The polymerase chain reaction was used to prepare the $^{32}p$ labeled probes used to identify colonies which contained plasmids bearing repeat DNA. Reaction mixtures consisted of 100 µl Volume using 0.75 µg of Hind III digested Chromosome 8 library DNA template, 200 µM each of dCTP, dGTP, dATP, dTTP, 100 µCi of alpha $^{32}p$ dCTP, 1 µM each of the two previously described alphoid-specific synthetic oligonucleotide primer mixtures of Example 2 and 2.5 units Taq polymerase in a buffer containing 20 mM Tris-HCl (pH 8.3), 50 mM KCl, 1.5 mM $MgCl_2$, and 0.01% gelatin. The reaction mix was overlaid with 100 µl of sterile mineral oil and the amplification was performed automatically using the Perkin Elmer Cetus (PEC) DNA Thermal Cycler as described above. The enzymatically amplified products were gel filtered on a Bio-Spin 30 column (BioRad, Richmond, Calif.), following the manufacturer's instructions, to remove unincorporated nucleotides, extracted with phenol-chloroform, precipitated with ethanol and resuspended in 100 µl of sterile water. The radio-labeled probe mixture was heated at 100° C. for 5 minutes followed by rapid cooling on ice. The hybridization mix consisted of $4.5 \times 10^6$ cpm of the denatured probe diluted in 10 mls of freshly prepared hybridization solution (described below) which was then added to each bag containing a single, prehybridized filter.

Example 12. Cloning Colonized Chromosome Library, Forming Hybrids, Identifying Sequences, Sampling Colonies, Culturing add Extracting Screening of library DNA containing flow sorted, Hind III restricted Chromosome 8 DNA cloned into the Bluescribe (pBS) plasmid vector (Stratagene) began with the preparation of several nitrocellulose filter membranes carrying bacterial colonies containing the library DNA. The method used to prepare these filters, or colony lifts, has been previously described (Sambrook, et al. "Molecular Cloning: A Laboratory Manual", pp. 1.90–1.104). Ten colony lifts, approximately 1000 bacterial colonies per filter, were prehybridized overnight at 68° C. with continuous agitation in individual seal-a-meal bags containing a hybridization solution consisting of 1.5 X SSPE (0.27M NaCl, 15 mM sodium phosphate (pH 7.7), 1.5 mM EDTA), 0.5% (w/v) BLOTTO (Carnation non-fat powdered milk), and 1% (w/v) SDS.

After introduction of the labeled probe described in Example 11, the hybridization was allowed to proceed overnight at 68° C. with continuous agitation. The next day, the unhybridized probe was removed by washing the filter membrane batchwise (three times, each for 5 minutes at room temperature with vigorous agitation) in a low stringency solution consisting of 2 X SSC (0.3M NaCl/30 mM sodium citrate), pH 7.0 and 0.1% sodium dodecyl sulfate (SDS). Stringency was increased by washing the filters (two times, each for 10 minutes at 55°–60° C. with vigorous agitation) in a solution consisting of 1 X SSC 9 pH 7.0) and 0.1% SDS. Following the last high stringency wash, the filters were wrapped in Saran wrap and exposed to X-ray film (XAR-5, Eastman Kodak, Rochester, N.Y.) at −70° C. overnight.

Each of the 10 filters produced several discrete, intense hybridization signals. After matching the orientations of the filters with their respective master nutrient agar plates, sixty bacterial colonies which had produced strong hybridization signals on film were selected for further analysis. In order to isolate DNA from each of the possible clones for size characterization, a single colony was picked off the agar plate and used to inoculate 2 mls of 2 YT nutrient broth (1.6% (w/v) Tryptone, 1% (w/v) yeast extract, 0.5% (w/v) NaCl) containing 200 µg/ml of ampicillin for selection. The cultures were grown at 37° C. overnight with vigorous agitation.

As a means of further reducing the number of candidate clones and enriching for those clones with the highest alphoid content, the candidate clones were examined in a more quantitative fashion for strength of hybridization to an alphoid probe.

Plasmid DNA was extracted and purified (Sambrook, et al. "Molecular Cloning: A Laboratory Manual", pp. 1.25–1.28) from each of the sixty cell cultures grown up from colonies selected in the library screening. Dot blot analysis was employed in an effort to select only those clones which produced true hybridization signals when probed with the labeled amplified alpha satellite sequences. An aliquot (3 µl) of alkaline lysis purified plasmid DNA was denatured in the presence of 50 mM sodium hydroxide and then dotted on a nitrocellulose membrane filter (Schleicher and Schuell, Keene, N.H.) presoaked in 10 X SSC (150 mM sodium citrate, 1.5M NaCl). The filter was allowed to air dry and then baked at 80° C. under vacuum for 15 hours.

The filter, or dot blot, was prehybridized overnight at 68° C. with continuous agitation in an hybridization solution consisting of 1.5 X SSPE (0.27M NaCl, 15 mM sodium phosphate (pl 17.7), 1.5 mM EDTA), 0.5% (w/v) BLOTTO (Carnation non-fat powdered milk), and 1% (w/v) SDS. Biotinylated amplified alpha satellite DNA sequences, generated from Hind III restricted pBS-Chromosome 8 library DNA as template by the PCR method as described above were used to probe the blotted DNA. The biotinylated probes (40 μl of a 100 μl PCR reaction) were denatured at 70° C. for 5 minutes in the presence of 5 μg carrier DNA (sonicated salmon sperm DNA) and 50% formamide/0.3M NaCl/30 mM sodium citrate/10% dextran sulfate, pH 7.0. The denatured probe mixture was rapidly cooled on ice, added to 20 m/s of freshly prepared hybridization solution (described above), and subsequently added to the seal-a-meal bag containing the prehybridized dot blot. Hybridization proceeded at 65° C. for 2.5 hours with continuous agitation. Unbound probes were removed by washing the filter membrane (three times, each for 5 minutes at room temperature with vigorous agitation) in a low stringency solution consisting of 2 X SSC (0.3M NaCl/30 mM sodium citrate), pH 7.0, and 0.1% sodium dodecyl sulfate (SDS). Stringency was increased by washing the filters (two times, each for 10 minutes at 55°–60° C. with vigorous agitation) in a solution consisting of 1 X SSC (pH 7.0) and 0.1% SDS.

Detection of hybridized biotinylated alpha satellite sequences to homologous target sequences present in the blotted DNA followed. This process for detecting signal is based on the strong binding of streptavidin to biotin. The filter was briefly rinsed in TTBS (0.1% (v/v) Tween 20, 100 mM Tris-HCl (pH 7.5), 0.9% NaCl) to remove the previous wash solution. In order to prevent nontarget sites on the filter from reacting with the detection reagents, the filter was blocked by incubating it in fresh TTBS for 30 minutes at room temperature with gentle shaking. During this period the horseradish peroxidase (HRP)-streptavidin conjugate (Vectastain ABC Kit, Vector Labs, Burlingame, Calif.) was prepared according to directions provided. The HRP-streptavidin conjugate was added to the pre-blocked filter and incubated for 30 minutes at room temperature with gentle shaking. Excess conjugate was removed through a series of washes in TTBS (four changes of buffer over a 15 minute period at room temperature with gentle shaking). Following the last wash a freshly prepared substrate solution (0.1M Tris-HCl (pH 7.5), 0.8 mg/ml diaminobenzidine tetrahydrochloride (DAB), 0.01% hydrogen peroxide, 0.4 mg/ml nickel chloride) was added and rapid signal development followed. The developed dot blot was rinsed with two changes of distilled $H_2O$ to stop the reaction and then allowed to air dry. Over half of the clones assayed through this method produced signal but only twenty-one clones were selected for further analysis. These clones produced strong hybridization signals in the dot blot analysis, clearly indicating the presence of alphoid sequences in each one.

These 21 candidate clones were further characterized by determining the size of the human DNA restriction fragment they contained. Characterization of the insert sizes in the twenty-one clones were made possible through the use of restriction enzyme analysis. The pBS-Chromosome 8 library DNA had been prepared by ligating a variety of different sized Hind III-cut Chromosome 8 DNA fragments to Hind III-cut BlueScribe plasmid vector. Restriction digests of the isolated clones with Hind III release the Chromosome 8 DNA inserts from the vector backbone. The digests consisted of 5 μl of alkaline lysis purified plasmid DNA, a low salt buffer (50 mM NaCl, 10 mM Tris-HCl (pH 7.5), 10 mM $MgCl_2$), and 2 μl of Hind III (20 units/μl, New England Biolabs). The digestions were allowed to proceed at 37° C. for two hours. The Hind III restricted DNAs were gel electrophoresed (1% agarose in 1 X TAE running buffer (Sambrook, et al. "Molecular Cloning: A Laboratory Manual," pp. 6.3–6.13.) in the presence of size standards. Hind III digestion of these plasmids identified the presence of one or more Chromosome 8 DNA fragments per clone which ranged in size from approximately 120 base pairs up to 9 kilobase pairs.

Several of the clones containing centromeric sequences specific for Chromosome 8 contained more than a single Hind III insert, making it necessary to identify which of these cloned fragments was responsible for hybridization to the labeled amplified alpha satellite DNA probes. Southern analysis made it possible to determine the alphoid content in each of the clones. Since the insert sizes covered a broad range (approximately 120 base pairs up to 9 Kilobase pairs) and the efficiency of transfer of gel electrophoresed DNA fragments onto a filter membrane is largely dependent on relative size of the fragments, this process required that two different types of filter membranes be used. Large DNA fragments (>1 Kilobase pairs), from each of the twenty-one clones were separated on an agarose gel and transferred to a nitrocellulose filter membrane (Schleicher and Schuell, Keene, N.H.) with relatively good efficiency while smaller DNA fragments (<1 Kilobase pairs), found only in eleven of the clones, were separated on a polyacrylamide gel and transferred to a nylon filter membrane (Zetaprobe, Bio-Rad, Richmond, Calif.).

The restriction digests of each clone consisted of an aliquot (3 μl) of alkaline lysis Purified plasmid DNA, a low salt buffer (50 mM NaCl, 10 mM Tris-HCl (pH 7.5), 10 mM $MgCl_2$), and 2 μl of Hind III (20 units/μl, New England Biolabs, Beverly, Mass.). The reaction proceeded for several hours at 37° C. and then gel electrophoresed either in 1% agarose/1 X TAE running buffer (Maniatis et al., Cold Spring Harbor), or 6% polyacrylamide/1 X TBE running buffer (Maniatis et al., Cold Spring Harbor, in the presence of size standards until transfer of the fragments onto nitrocellulose was done according to directions provided with the Vacugene Vacuum Blotting System (Pharmacia LKB). The membrane was baked at 80° C. under vacuum for 1.5 hours. Transfer of the polyacrylamide gel separated DNA fragments onto nylon was done according to directions provided with the Semi-Dry Electroblotter (JKA-Biotech, Denmark). The nylon membrane did not require baking.

Both filter membranes were prehybridized in a hybridization solution consisting of 1.5 X SSPE (0.27M NaCl, 15 mM sodium phosphate (pH 7.7), 1.5 mM EDTA), 0.5% (w/v) BLOTTO (Carnation non-fat powdered milk), and 1% (w/v) SDS. Prehybridization proceeded at 68° for 24 hours (nitrocellulose filter) or 72 hours (nylon filter) with continuous agitation. Biotinylated amplified alpha satellite DNA probes generated using Hind III restricted pBS-Chromosome 8 DNA as template and the degenerate primers (U. Weier, LLNL) were used to probe each blot. The biotinylated probes (40 μl of a 100 μl PCR reaction) were denatured at 70° C. for 5 minutes in the presence of 50% formamide/ 0.3M NaCl/30 mM sodium citrate/10% dextran sulfate, pH 7.0, and 5 μg of carrier DNA (sonicated salmon sperm DNA). The denatured probes were rapidly cooled on ice and added to 20 mls of freshly prepared hybridization solution (described above). Hybridization proceeded at 68° C. for three hours. Unbound probes were removed by washing the filter membrane (four times, each for 5 minutes at room temperature with vigorous agitation) in a low stringency solution consisting of 2 X SSC (0.3M NaCl/30 mM sodium citrate, pH 7.0) and 0.1% sodium dodecyl sulfate (SDS). Stringency was increased by washing the filters (two times, each for 10 minutes at 55°–60° C. with vigorous agitation) in a solution consisting of 1 X SSC (pH 7.0) and 0.1% SDS.

Detection of hybridized biotinylated alpha satellite sequences to homologous target sequences present on each filter followed. This process for detecting signal is based on the strong binding of streptavidin to biotin, and was carried out as described above in this example.

Southern analysis of the nitrocellulose membrane identified sixteen clones in which a single non-vector fragment produced a strong hybridization signal. The remaining clones each had two hybridization signals-indicating the presence of alphoid sequences in both Hind III fragments. The fragments identified as containing alphoid sequences can be classified by size:

1.2 Kbp, 1.5 Kbp 1.9 Kbp 2.3 Kbp, 2.5 Kbp

3 Kbp 3.5–3.8 Kbp 5.5–5 Kbp

9 Kbp

Southern analysis of the nylon membrane also produced strong hybridization signals-none of which were associated with a DNA fragment smaller than 1200 base pairs in length.

Example 13. Labeling Each Vector DNA Forming a Probe Class

Each fermented and extracted vector DNA material produced as described in Example 12 was labeled by the polymerase chain reaction (PCR) procedure of Ex. 7 so that 21 probe compositions were prepared.

Example 14. Hybridize Each Probe with Sample of Genome as Target

Each of the probe compositions of Example 12 was hybridized to a target sample of the human genome.

The target sample and the hybridization procedure were described in Example 8.

Example 15. Identify Repeated DNA Sequences, Culture and Extract

The product hybridized samples of Example 13 were examined and a single DNA sequence containing repeated sequences characteristic of Chromosome 8 was separated using the procedure of Example 9. As in Example 9, no DNA sequences were separated. Recordkeeping was used to determine which of the probes was derived from specific colonies. When the colony to be grown up for further use is identified, the original colony is sampled and cultured.

There is little difference in the growth of the plasmid bearing bacteria and the phage infected bacteria, as those skilled in the art appreciate. Once the culture is identified, the DNA extraction is carried out as above described in Example 11.

Cultures of *E. coli* bearing the appropriate plasmids were prepared as follows:

Bacteria bearing the appropriate plasmid were streaked onto the surface of a YT agar plate containing 200 µg/ml of ampicillin and allowed to grow overnight at 30° C. A single colony from this plate was transferred to 500 milliliters of 2 YT media in a 2.4 liter Fernbach flask and allowed to grow overnight at 30° C. at a constant agitation rate of 200 cycles. As in Example 11, cells were harvested by centrifugation and the plasmid DNA was extracted.

The presently preferred plasmid probe for the centromere of chromosome 8 has a vector of approximately 2800 base pairs, and an insert of approximately 9000 base pairs.

Example 16. Transamination with Chaotrope

The extent of bisulfite catalyzed transamination which can be achieved involving single stranded DNA that can hybridize to form double-stranded, complementary DNA was found to be limited by the formation of the double-stranded form of the DNA substrate. Those deoxycytidine residues which participate in base-pairing interactions do not undergo transamination. This limitation was observed to be more extreme in cases where the DNA sequence to be transaminated was composed largely of relatively small repeats, as in the case of cloned alphoid DNA. However, as the concentration of complementary strands increases, the rate of their hybridization also increases. Inclusion of chaotrope in the transamination reaction was evaluated as a method to decrease the rate at which DNA renatures in this reaction. The efficacy of the method was tested on salmon sperm DNA.

Salmon sperm DNA (Sigma Cat. #D-1626) was dissolved in water at a concentration of 8 mg/ml. The DNA was diluted with water to a concentration of 2 mg/ml and a 2 ml aliquot was sonicated. The solution was contained in a 5 ml polypropylene tube which was immersed in a dry ice/ethanol bath to prevent boiling during sonication. The microtip of the sonication device was immersed in this solution until the tip was 2–5 mm from the bottom of the tube. Sonication was carried out at an output power of 25–30 watts, discontinuously, with an 80% duty cycle (on 80% of the time, off 20% of the time), for a period of 5 minutes. Following sonication, the DNA was precipitated by the addition of 0.2 mls of 3M sodium acetate (pH 5.5) and 4 mls of ethanol. The precipitate is recovered by centrifugation for 5 minutes at 8,000 x g and vacuum dried.

To prepare bisulfite buffer with no chaotrope, 1.7 ml of concentrated HCl was slowly added to 2 ml of deionized $H_2O$ on ice. 1 ml fresh ethylene diamine (Sigma Cat. #E-4379) was then slowly added on ice. After dissolution of the ethylene diamine, the solution was warmed to room temperature and 0.475 g sodium metabisulfite (Aldrich Cat. #25, 555-6) was added. Concentrated HCl was then slowly added to the bisulfite mixture until the pH reached 7.0 and the volume of the solution was adjusted to 5.0 ml.

To prepare bisulfite buffer with the chaotrope, trifluoroacetic acid (TFA), 1.53 ml of trifluoroacetic acid was added to 2.5 ml of deionized $H_2O$ on ice and the mixture was allowed to cool for 10 minutes. 0.87 ml of ethylene diamine (Sigma Cat. #E-4379) was then slowly added on ice. After dissolution of the ethylene diamine, the solution was warmed to room temperature and 0.475 g sodium metabisulfite (Aldrich Cat. #25, 555-6) was added. The solution was warmed to 45° C. to dissolve the sodium metabisulfite. The pH was adjusted to 7.0 by the addition of trifluoroacetic acid and the volume of the solution adjusted to 5.0 ml. A 100 milligram/milliliter solution of hydroquinone in absolute ethanol was prepared and added to the bisulfite buffer at a rate of 50 µl of hydroquinone solution per 5 ml of bisulfite solution.

To transaminate DNA, 1 mg of sonicated DNA segments was resuspended in 300 µl of water. The DNA segments were denatured by boiling at 100° C. for 5 minutes then quickly chilled in an ice water bath. The transamination reaction was initiated by the addition of 2.7 ml of bisulfite buffer or bisulfite buffer with chaotrope. Reaction in the aqueous bisulfite buffer without chaotrope was allowed to proceed for 2 days at 37° C. Reaction in bisulfite buffer with chaotrope was allowed to proceed for 18 hours at 45° C. The DNA solution in each case was desalted by routine dialysis against 20 mM sodium acetate (pH 7). After dialysis, 0.1 ml of 3M sodium acetate (pH 5.5) was added. Each aminated DNA product was precipitated with 2.5 ml of ethanol and recovered after centrifugation at 8,000 x g for 10 minutes.

The pellets were vacuum dried and rehydrated at a concentration of 3 mg/ml in water.

The extent of transamination of each aminated DNA product (dC) was determined by enzymatic digestion of the dC followed by separation of the resulting nucleosides on a FPLC chromatography system (Pharmacia LKB, Piscataway, N.J.). 5–10 μg of aminated DNA was diluted with water to 50 μl and the DNA purified on a spin column containing Sephadex G-50 (3 Prime→5 Prime catalog #5301–755608, West Chester Pa.). The DNA was then dried and 12.5 μl of 2 X DNase 1 buffer (20 mM TRIS, 10 mM $MgCl_2$, pH 7.5) and 0.5 μl of deoxyribonuclease 1 (DNase 1) (BRL, 2 mg/474 μl, >10,000 μ/mg) added to the DNA and the solution incubated in a 37° C. water bath for 1 hr. 50 μl of 2 X PDl/Alk. Phos. buffer (100 mM TRIS, 200 mM NaCl, 28 mM $MgCl_2$, 2 mM $ZnCl_2$, pH 9.0), 19 μl of water, 5.0 μl of phosphodiesterase 1 (PDl) (Pharmacia LKB, 1,000 μ/ml dissolved in 1 X PDl/Alk. Phos. buffer), and 1.0 μl calf intestinal alkaline phosphatase (Promega, 10,000 μ/ml) was then added and the solution incubated for an additional 2 hr at 37° C. The digested sample was then applied to a MinoRPC column (Pharmacia, LKB) and a linear gradient between buffer A (97.5:1 ion-pairing buffer:methanol, ion-pairing buffer=50 mM $KH_2PO_4$, 0.05% hexanesulfonic acid, pH 7.0) and buffer B (50:50 ion-pairing buffer:methanol) used to elute the sample (a 0.8% increase in buffer B/min at a flow rate of 0.37 ml/min until 40% buffer B was reached, followed by a 3% increase in buffer B/min to 100% buffer B at a flow rate of 0.3 ml/min) while recording the DNA elution profile by absorbance. Each of the 4 natural deoxynucleosides and the transamination product of deoxycytidine eluted separately and the amount of deoxycytidine transaminated was determined from the relative areas under the deoxycytidine and transaminated deoxycytidine peaks in the elution profile.

The deoxycytidine residues in the salmon sperm DNA aminated in the absence of chaotrope were derivatized at a rate of 15.2%. The deoxycytidine residues in the salmon sperm DNA aminated in the presence of chaotrope were derivatized at a rate of 67%.

This result clearly demonstrates that the use of chaotrope can significantly increase the extent of amination which can be achieved via the transamination reaction.

Example 17. Transamination of Sequences Complementary to Centromere of Chromosome #8

To examine the performance of various alphoid DNA containing plasmids which had been recovered from the pBS8 library produced in Example 12 and from the M13 clones produced in Example 5 in in situ hybridizations using the biotin-streptavidin format, it was necessary to modify these DNAs with biotin. This was accomplished with the two step procedure of first derivatizing (transaminating) deoxycytosine residues in the plasmid DNA with ethylenediamine via the bisulfite catalyzed transamination reaction described above, and secondly, attaching biotin to the newly introduced, active amine by reaction with the succinimidyl ester of biotin.

To determine whether higher degrees of biotin substitution would improve probe performance in the assay, some of the DNAs were transaminated both in the presence and absence of the chaotrope trifluoracetic acid.

Cultures of plasmids 1-1, 2-2 and 10-4 were as follows. Bacteria bearing the appropriate plasmid were streaked onto the surface of YT agar plate containing 200 μg/ml of ampicillin and allowed to grow overnight at 30° C. A single colony from this plate was transferred to 500 milliliters of 2 YT media in a 2.4 liter Fernbach flask and allowed to grow overnight at 30° C. at a constant agitation rate of 200 cycles/minute.

Cultures of the M13 clones 1-1 and 2-2 were prepared as follows. E. coli JM101 was cultured overnight at 37° C. in YT Broth. the JM101 culture was diluted ¹/₁₀₀ in 3 ml of YT Broth and allowed to grow for 3 hours. $10^7$ phage were added to 0.5 ml of this culture and allowed to grow for 3 hours and then transferred to 500 ml of YT Broth in a 2.4 liter Fernbach flask. This culture was allowed to grow overnight at 37° C. with constant agitation. At this point, the bacterial cells contain significant amounts of the circular double-stranded (replicative form) of the bacteriophage DNA. THis form of the DNA can be recovered by the same procedure as is used for the recovery of plasmid DNA.

DNA was extracted from all of the cultured cell masses as described in Example 10 above. The purified DNA was disrupted into small fragments of approximately 300 base pairs by sonication using a Branson Sonifer 450 (Danbury, Conn.). DNA from the plasmid preparations was sonicated in 2 mls of water at concentrations ranging from 100 to 350 μg/ml. The solution was immersed in this solution until the tip was 2–5 mm from the bottom of the tube. Sonication was carried out at an output power of 25–30 watts, discontinuously, with an 80% duty cycle (on 80% of the time, off 20% of the time), for a period of 5 minutes. Following sonication, the DNA was precipitated by the addition of 0.2 mls of 3M sodium acetate (pH 5.5) and 4 mls of ethanol. The precipitate is recovered by centrifugation for 5 minutes at 8,000 x g and vacuum dried.

To chaotropically transaminate probe DNA, 200–500 μg of sonicated DNA was resuspended in 100 μl of water. The DNA was denatured by boiling at 100° C. for 5 minutes then quickly chilled in an ice water bath. The transamination reaction was initiated by the addition of 900 μl of bisulfite buffer or bisulfite buffer with chaotrope as described in Example 15 above. Reaction in bisulfite buffer was allowed to proceed for 2 days at 37° C. Reaction in bisulfite buffer with chaotrope was allowed to proceed for 18 hours at 45° C. The DNA solution was desalted by routine dialysis against 20 mM sodium acetate (pH 7). After dialysis, 0.1 ml of 3M sodium acetate (pH 5.5) was added. The aminated DNA was precipitated with 2.5 ml of ethanol and recovered after centrifugation at 8,000 x g for 10 minutes. The pellets were vacuum dried and rehydrated at a concentration of 700–1400 μg/ml in 0.2M 3-[N-morpholino] propane sulfonic acid (MOPS) buffer, pH 7.4.

Biotin was added to the aminated DNA by reaction of the DNA with the succinimidyl ester of biotin. The aminated DNA solution was denatured by boiling for 5 minutes then quickly cooling in an ice water bath. An estimated 100 fold molar excess of sulfosuccinimidyl-6-(biotinamido) hexanoate (Pierce catalog #21335 C, Rockford, Ill.), as a 0.2M solution in dimethyl sulfoxide, was then added to the aminated DNA. The amount of aminated nucleotide was in all cases estimated to be 5% of the total moles of nucleotide present in the sample. This reaction was allowed to proceed overnight at room temperature with constant agitation. DNA was precipitated from the reaction by the addition of 0.1 volume of sodium acetate (pH 5.5) and 3 volumes of ethanol. The precipitate was recovered by centrifugation. The precipitate was rehydrated in 100 μl of water and then desalted on a BioRad S30 column (Rockville Centre, N.Y.). DNA from the eluant was precipitated by the addition of 0.1 volume of sodium acetate (pH 5.5) and 3 volumes of ethanol. Precipitate was collected by centrifugation and vacuum dried. The DNA was resuspended at approximately 1 milligram/ml, A 5 μl portion of the probe solution was diluted into 600 μl of 50 mM NaOH, The absorbance of this solution at 260 nanometers was determined in order to provide an accurate probe concentration.

Performance of these probes was evaluated in the in situ hybridization assay described in Example 4 above. From a comparison of the signal intensities produced by probes transaminated without chaotrope to the signal intensities produced by probes transaminated with chaotrope we conclude that biotinylated probes prepared by transamination in the presence of the chaotrope trifluoroacetic acid produce more intense signals at lower DNA concentrations than probes produced by transamination in the absence of the chaotrope.

Example 18. Direct and Indirect Labeling of Transaminated Sequences with Fluorophore Groups and Use in In Situ Hybridization The ability of a DNA sequence produced as above described to function in in situ hybridization assays which use biotin-avidin interactions and a fluorescent endpoint is a useful property. However, there are a wide variety of methods for visualizing probes. To demonstrate the general utility of probes prepared from DNA sequences produced by the practice of the present invention, the following example is provided which show illustratively that one of those sequences, identified as 10-4 of Example 12 above is readily adapted for use in fluorescent assays in which the probe is direct labeled with fluorophores.

(A) Direct and Indirect Labeling DNA Sequence 10-4 To Centromere Of Chromosome #8

The DNA sequence from plasmid 10-4 was prepared (amplified) by fermentation. Bacteria containing the plasmid 10-4 were streaked onto a YT agar plate containing 200 μg/ml of ampicillin. A single colony from this plate was transferred into 2 ml of 2 YT broth and allowed to grow overnight at 30° C. with agitation. This bacterial suspension served as the seed stock for the fermentation process previously described in Example 1. Harvesting of the fermented culture and extraction of the DNA sequence were as previously described in this Example. Fermentation yielded a cell mass of 204 grams. Extraction of 122 grams of this pellet yielded 60 milligrams of plasmid DNA. 1 milligram of the resulting plasmid 10-4 DNA sequence was sonicated as previously described in Example 3. 1 milligram of this sonicated DNA was resuspended in 1 ml of distilled water. The DNA was denatured by boiling for 5 minutes and quickly cooling on ice.

9 mls of bisulfite buffer with chaotrope (previously described in Example 15) were added and a transamination reaction with chaotrope as described in Example 15 was allowed to proceed for 2 days at 37° C. DNA product which resulted was desalted by routine dialysis against 10 mM sodium borate (pH 8.0). This resulting DNA was precipitated by the addition of 0.1 volume of 3M sodium acetate (pH 5.5) and 2.5 volumes of ethanol, and the precipitated DNA was resuspended in water at a concentration of 1 milligram/milliliter.

Forty micrograms of the resulting aminated DNA sequence 10-4 to the centromere of chromosome #8 was dried into a 2 ml tube and then resuspended in 362 μl 0.20M MOPS (3-[N-Morpholino] propanesulfonic acid), pH 7.4. The fluorescent compound 5-(and -6) carboxytetramethyl-rhodamine (CTMR), succinimidyl ester was dissolved in dimethylformamide to 30 mM. A 150-fold molar excess of this fluorophore was added to the aminated DNA, in this case 37.9 μl of 30 mM CTMR. This labeling reaction proceeded in darkness at room temperature with the tube rotating overnight.

The purification of the labeled probe away from the excess fluorophore was a subsequent three step procedure. The first step was an ethanol precipitation. Any remaining ethanol was evaporated from the precipitated pellet, then the probe was resuspended in 300 μl water. This solution was passed over a Sephadex G-25 column 28 cm high and 1 cm in diameter. The desired fraction (the column void volume) was eluted with water and dried to reduce the total volume. A second ethanol precipitation completed the purification and the dried pellet was resuspended in 300 μl water. An absorbance spectrum of the resulting direct label probe composition showed 3.1% of the total nucleotides were labeled.

Biotin was added to the aminated DNA by reaction of the DNA with the succinimidyl ester of biotin. A 200 μg aliquot of transaminated 10-4 DNA solution was prepared in 485 μl of 0.2M MOPS buffer, pH 7.4, denatured by boiling for 5 minutes then quickly cooling in an ice water bath. Sulfosuccinimidyl-6-(biotinamido) hexanoate (Pierce catalog #21335 C, Rockford, Ill.), was prepared as a 0.2M solution in dimethyl sulfoxide. A 15.2 μl aliquot of the biotin solution was added to the DNA solution, and the reaction was allowed to proceed overnight at room temperature with constant agitation. DNA was precipitated from the reaction by the addition of 0.1 volume of sodium acetate (pH 5.5) and 3 volumes of ethanol. The precipitate was recovered by centrifugation. The precipitate was rehydrated in 100 μl of water and then desalted on a BioRad S30 column (Rockville Centre, N.Y.). DNA from the eluant was precipitated by the addition of 0.1 volume of sodium acetate (pH 5.5) and 3 volumes of ethanol. Precipitate was collected by centrifugation and vacuum dried. The DNA was resuspended at approximately 1 milligram/ml. A 5 μl portion of the probe solution was diluted into 600 μl of 50 mM NaOH. The absorbance of this solution at 260 nanometers was determined in order to provide an accurate probe concentration.

(B) In Situ Hybridization Using 10-4 CTMR Probe Composition 16 ng of the direct label probe composition of above was dried into a 0.5 ml tube with a tight-fitting cap. The probe was resuspended in 10 μl of 55% formamide/10% dextran sulfate/0.15M NaCl/15 mM sodium citrate, pH 7.0, with 4.5 μg sonicated human placental DNA being added as blocker. This hybridization mixture was denatured by placing the tube in a 70° C. water bath for 5 minutes.

A target slide which was prepared as described in Example 4 above was denatured for 3 minutes was denatured for 3 minutes in a 70° C. solution of 70% formamide/2 XSSC and then dehydrated by passing successively through 70%, 85%, and 100% ethanol baths (2 minutes each). A drop of the hybridization mixture was pipetted onto the slide and the drop was covered with a coverslip. The coverslip was sealed onto the slide with rubber cement. The hybridization was allowed to proceed overnight in a dark, humidified 37° C. chamber.

The next day the residual unbound probe was removed by washing the slide (three times, each for 15 minutes at 45° C.) in 50% formamide/0.3M NaCl/30 mM sodium citrate, pH 7.0. A single wash (15 minutes at 45° C.) in 0.3M NaCl/30 mM sodium citrate (2 XSSC, pH 7.0), followed. The slide was next washed in 0.1M sodium phosphate/0.1% NP40 detergent (PN buffer) (15 minutes at 45° C.). Finally, the slide was washed twice in PN buffer (2 minutes at room temperature), and air dried. 7.5 μl of 1 μg/ml DAP1 in an antifade solution was placed over the target cells and a coverslip was placed over that.

The results obtained are shown in the following Table VI:

TABLE VI

Results of In Situ Hybridization with Fluorophore Direct Label Probe

| Hybridization Conditions | | Visual Description | |
| --- | --- | --- | --- |
| CTMR Probe | Concentration (ng/10 µl) | Intensity (1) | Specificity (2) |
| #10-4 (9 Kbp insert) | 16* (3) | +++ | +++ |

Table footnotes:
(1) Intensity: (−) not visible, (+) barely visible, (++) fairly visible, (+++) bright, (++++) very bright, (NE) cannot be evaluated
(2) Specificity: (−) none apparent, (+) low specificity, (++) reasonable specificity, (+++) good specificity, (NE) cannot be evaluated
(3) * carrier DNA present (4.5 µg human placental DNA/10 µl)

Based on the results shown in. Table VI, it was concluded that the so produced direct label probe composition is well suited for use in in situ hybridization enumerations of specific chromosome centromeres using fluoroscopic analysis.

Example 19. A Centromere 12-Specific DNA Probe (A) Recovery of Centromere 12-Specific DNA Clones From The PBS 12 Library The production of expanded seed stocks and the production of large quantities of DNA by fermentation and extraction from the original library for chromosome 12 provided by LLNL was accomplished as described in Example 1 of Bittner et al. patent U.S. Ser. No. 585,876 and in Example 1 of aforereferenced Bittner et al. U.S. Ser. No. 762,912 filed on even date herewith.

Screening of library DNA containing flow sorted, Hind III restricted Chromosome 12 DNA cloned into the Bluescribe (pBS) plasmid vector (Stratagene) began with the preparation of several nitrocellulose filter membranes carrying bacterial colonies containing the library DNA. Eleven colony lifts, approximately 1000 bacterial colonies per filter, prepared as in Example 12 above were probed as described in Example 12 above. The radioactive probe used was prepared by subjecting 0.75 µg of Hind III digested chromosome 12 library DNA to a PCR reaction containing $^{32}$PdCTP, as described in Example 11 above.

Each of the 11 filters produced several discrete, intense hybridization signals. After matching the orientations of the filters with their respective master nutrient agar plates, sixty bacterial colonies which had produced strong hybridization signals on film were selected for further analysis. Preparation of cloned DNA from each of these colonies, and determination of the size of the Hind III inserts in each of these colonies, was accomplished as described in Example 12. Hind III digestion of these plasmids identified the presence of one or more Chromosome 12 DNA fragments per clone which ranged in size from approximately 200 base pairs up to 6 kilobase pairs.

Dot blot analysis of these clones to determine which of them contained DNA complementary to chromosome 12 alphoid sequences was accomplished by the method described in Example 12. The biotinylated probe DNA utilized was prepared by subjecting 0.75 µg of Hind III digested chromosome 12 library DNA to the PCR procedure described in Example 3.

All of the clones assayed through this method produced signal; none appeared to be stronger than any of the others. Thirteen clones, each containing Chromosome 12 fragments ranging from 1.3 Kbp to 6 Kbp in size, were selected for further analysis.

Two of the thirteen clones contained more than a single Hind III insert, making it necessary to identify which of these cloned fragments was responsible for hybridization to the labelled, amplified alpha satellite DNA probes. Southern analysis as described in Example 12, using a biotinylated made it possible to determine the alphoid content in each clone.

Southern analysis of the cloned identified a single non-vector fragment in each of the thirteen clones which was responsible for producing a strong hybridization signal. The fragments identified as containing alphoid sequences can be classified by size:

1.3–1.4 Kbp
1.8 Kbp
2.3–2.5 Kbp
3 Kbp
3.5–3.8 Kbp
4.3–4.5 Kbp
5.5–6 Kbp (B) Performance Of Cloned, Centromere 12-Specific DNAS Enzymatically Derivatized With Biotin In order to examine the performance of various alphoid DNA containing plasmids which had been recovered form the pBS8 library in in situ hybridizations using the biotin-streptavidin format, it was necessary to modify these DNAs with biotin. The PCR was used to prepare the biotin labelled probes used to identify a clone or clones suitable for use as a Chromosome 12 centromere specific probe. A 0.75 µg aliquot of Hind III digested DNA template, from each clone was subjected to the PCR protocol described in Example 3. The PCR products were extracted with phenol-chloroform and then gel filtered on Bio-Spin 30 column (BioRad, Richmond, Calif.) following the manufacturer's instructions, to remove unincorporated nucleotides.

Three µl aliquots of a 1:50 dilution of each of the purified, biotinylated clones were evaluated in an in situ hybridization assay.

The hybridization mix that was placed on each slide was always 55% formamide/10% dextran sulfate/0.15M NaCl/ 15 mM sodium citrate, pH 7.0. The mix contained 3 µl of the diluted PCR reaction mixture and 0.5 µg of sonicated salmon sperm DNA added as carrier. Ten microliters of the completed hybridization mixture were denatured by heating at 70° C. for 5 minutes and then rapidly cooled on ice. The mix was applied directly to the slide, covered with a glass coverslip whose edges were sealed with rubber cement, and allowed to hybridize overnight at 42° C. in a humidified chamber.

Results are shown in Table VII below:

TABLE VII

| | Qualitative Results | |
| --- | --- | --- |
| | Visual Description | |
| Clones | Intensity | Specificity |
| #1-1 (3.5 Kbp insert) | ++++ | ++++ |
| #1-3 (3.2 Kbp insert) | +++ | + |
| #1-4 (5.5–6 Kbp insert) | ++ | − |
| #2-1 (1.3–1.4 Kbp insert) | ++++ | + |
| #2-3 (2.5 Kbp insert) | ++++ | ++++ |

TABLE VII-continued

Qualitative Results

| Clones | Visual Description | |
|---|---|---|
| | Intensity | Specificity |
| #2-7 (1.3–1.4 Kbp insert) | ++ | + |
| #4-4 (1.8–2.0 Kbp insert) | +++ | ++ |
| #5-1 (4.3–4.4 Kbp insert) | +++ | + |
| #6-1 (4.5 Kbp insert) | ++ | – |
| #6-2 (2.5 Kbp insert) | ++++ | +++ |
| #8-2 (2.5 Kbp insert) | +++ | ++ |
| #9-1 (1.3–1.4 Kbp insert) | ++ | + |
| #11-1 (3 Kbp insert) | ++ | – |

Table VII footnotes:
(1) Intensity: (–) not visible, (+) barely visible, (++) fairly visible, (+++) bright, ( ++++) very bright, (NE) cannot be evaluated
(2) Specificity: (–) none apparent, (+) low specificity, (++) reasonable specificity, (+++) good specificity, (NE) pannot be evaluated Based on these results, it is concluded that both good intensity and specificity with a probe derived from a single plasmid is obtained.

Based on the results from the evaluation of the biotinylated clones in the in situ hybridization assay clone 1-1 was selected for direct fluor labeling. A culture of plasmid 1-1 was prepared as follows. Bacteria bearing the plasmid were streaked onto the surface of YT agar plate containing 200 μg/ml of ampicillin and allowed to grow overnight at 30° C. A single colony from this plate was transferred to 500 milliliters of 2 YT media in a 2.4 liter Fernbach flask and allowed to grow overnight at 30° C. at a constant agitation rate of 200 cycles/minute.

DNA was extracted from the cultured cell masses using the protocol described in Example 10.

(C) Procedure For Directly Labelling Probe 1-1 to Centromere-12

Purified plasmid DNA 1-1 was disrupted into small fragments of approximately 300 base pairs by sonication as described above and the fragments of DNA were transaminated and covalently bound to the fluorescent compound CTMR to produce a probe composition as taught in Example 18 above. The probe composition is useful for in situ hybridization.

Other and further embodiments will be apparent to those skilled in the art from the preceding description and Examples. No unreasonable limitations or the like are to be drawn therefrom.

What is claimed is:

1. In an improved process for transaminating a polynucleotide under aqueous liquid phase conditions, said polynucleotide containing at least one deoxycytidine nucleotide per molecule, in the presence of a bisulfite catalyst and a reactive compound comprising the formula:

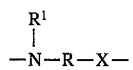

wherein:

X is a divalent radical selected from the class consisting of

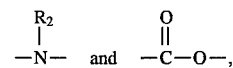

R is an alkylene radical containing 2 through 12 carbon atoms inclusive, and $R^1$ and $R^2$ are each independently selected from the class consisting of hydrogen and lower alkyl, the improvement which comprises carrying out the transaminating in the presence of a dissolved trihaloacetate chaotrope anion while maintaining a temperature of 20° to 60° C. and a pH of 4.5 to 7.5.

2. The process of claim 1 wherein said trihaloacetate chaotrope anion is selected from the group consisting of trifluoroacetate and trichloroacetate.

3. The process of claim 1 wherein said trihaloacetate chaotrope anion is trifluoroacetate.

4. The process of claim 1 which is carried out by the steps of:

(a) contacting said polynucleotide sequence in an aqueous solution containing as solutes (1) alkali metal bisulfite, and (2) at least one water soluble trihaloacetate salt wherein the trihaloacetate anion is selected from the group consisting of trifluoroacetate, trichloroacetate, and mixtures thereof, with a water soluble difunctional linking compound as said reactive compound, said linking compound containing two substituent functional radicals per molecule, one of which is selected from the group consisting of primary and secondary amino radicals, and the other of which is selected from the group consisting of primary amino radicals, secondary amino radicals, carboxylic acid radicals, and carboxylate radicals, said functional radicals each being bonded to an organic radical that contains at least two and not more than 20 carbon atoms;

(b) maintaining said solution at a pH of 4.5 to 7.5 and at a temperature of 20° to 60° C. until transamination of said deoxycytidine nucleotide(s) by an amino group of said linking compound occurs to a predetermined extent;

(c) dialyzing the resulting transaminated solution against an alkali metal lower alkanoate to separate therefrom substantially all non-alkanoate salt anions;

(d) precipitating from the so dialyzed solution the resulting transaminated nucleotide sequence product; and (e) separating said so precipitated product.

5. The process of claim 4 wherein said difunctional linking compound is ethylene diamine.

6. The process of claim 4 wherein said polynucleotide is selected from the group consisting of (a) at least one DNA sequence produced by the process of claim 1 and (b) a mixture of fragmented segments derived therefrom.

7. The process of claim 6 wherein (a) said polynucleotide comprises said mixture of fragmented segments and said mixture is transaminated to an extent such that 12 to 70 mole percent of all deoxycytidine nucleotides present therein are so transaminated by said linking compound, (b) said segments have average sizes of 150 to 600 base pairs, (c) the concentration of said segments in said solution is at least 20 micrograms per milliliter, and (d) said segments contain not less than about $1 \times 10^{10}$ complementary sequential copies per microgram of said segments.

8. The process of claim 4 wherein the resulting so transaminated nucleotide sequence product is reacted with a label group containing compound which incorporates a reactive radical that is reactive with a functional radical in said resulting so transaminated nucleotide sequence product that is derived from said linking compound.

9. In an improved process for transaminating a polynucleotide under aqueous liquid phase conditions, said polynucleotide containing at least one deoxycytidine nucleotide per molecule, in the presence of a bisulfite catalyst and a reactive compound comprising the formula:

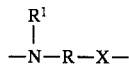

wherein:

X is a divalent radical selected from the class consisting of

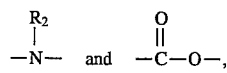

R is an alkylene radical containing 2 through 12 carbon atoms inclusive, and $R^1$ and $R^2$ are each independently selected from the class consisting of hydrogen and lower alkyl, the improvement which comprises carrying out the transaminating in the presence of a trifluoroacetate anion while maintaining a temperature in the range of 20° C. to 60° C. and a pH in the range of 4.5 to 7.5.

10. The method of claim 9 wherein pH is in the range of 6.5 to 7.5.

11. In an improved process for transaminating a polynucleotide under aqueous liquid phase conditions, said polynucleotide containing at least one deoxycytidine nucleotide per molecule, in the presence of a bisulfite catalyst and a reactive compound comprising the formula:

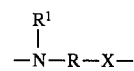

wherein:

X is a divalent radical selected from the class consisting of

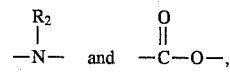

R is an alkylene radical containing 2 through 12 carbon atoms inclusive, and $R^1$ and $R^2$ are each independently selected from the class consisting of hydrogen and lower alkyl, the improvement which comprises carrying out the transaminating in the presence of a trichloroacetate anion at a concentration of less than 1M while maintaining a temperature in the range of 20° C. to 60° C. and a pH in the range of 4.5 to 7.5.

12. The method of claim 11 wherein pH is in the range of 6.5 to 7.5.

* * * * *